(12) United States Patent
Mehrara

(10) Patent No.: US 10,548,858 B2
(45) Date of Patent: Feb. 4, 2020

(54) INHIBITION OF SPHINGOSINE 1-PHOSPHATE RECEPTOR FOR TREATMENT AND PREVENTION OF LYMPHEDEMA

(71) Applicant: Memorial Sloan Kettering Cancer Center, New York, NY (US)

(72) Inventor: Babak Mehrara, Chappaqua, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/326,272

(22) PCT Filed: Aug. 17, 2017

(86) PCT No.: PCT/US2017/047291
§ 371 (c)(1),
(2) Date: Feb. 18, 2019

(87) PCT Pub. No.: WO2018/035292
PCT Pub. Date: Feb. 22, 2018

(65) Prior Publication Data
US 2019/0183818 A1   Jun. 20, 2019

Related U.S. Application Data

(60) Provisional application No. 62/376,496, filed on Aug. 18, 2016.

(51) Int. Cl.
*A61K 31/14*   (2006.01)
*A61K 31/397*   (2006.01)
*A61K 31/4245*   (2006.01)
*A61K 31/426*   (2006.01)
*A61K 31/137*   (2006.01)
*A61K 45/06*   (2006.01)
*A61K 31/40*   (2006.01)
*A61K 31/421*   (2006.01)
*A61P 7/00*   (2006.01)
*G01N 33/92*   (2006.01)
*A61P 7/10*   (2006.01)
*A61K 9/00*   (2006.01)

(52) U.S. Cl.
CPC .......... *A61K 31/137* (2013.01); *A61K 9/0019* (2013.01); *A61K 9/0053* (2013.01); *A61K 31/397* (2013.01); *A61K 31/40* (2013.01); *A61K 31/421* (2013.01); *A61K 31/426* (2013.01); *A61K 31/4245* (2013.01); *A61K 45/06* (2013.01); *A61P 7/00* (2018.01); *A61P 7/10* (2018.01); *G01N 33/92* (2013.01); *G01N 2405/08* (2013.01); *G01N 2500/00* (2013.01)

(58) Field of Classification Search
CPC ................ A61K 31/14; A61K 321/397; A61K 31/4245; A61K 31/426
USPC ........................... 514/643, 210.17, 364, 369
See application file for complete search history.

(56) References Cited

FOREIGN PATENT DOCUMENTS

WO   WO-2009117769 A1 * 10/2009   ........... A61K 31/137
WO   WO-2016028686 A1 *  2/2016   ........... A61K 31/405

* cited by examiner

*Primary Examiner* — Raymond J Henley, III
(74) *Attorney, Agent, or Firm* — Grimes & Yvon LLP

(57) ABSTRACT

Provided are methods of and compositions for treating or preventing lymphedema by administering a sphingosine 1-phoshate receptor modulator.

22 Claims, 22 Drawing Sheets

D

E

F

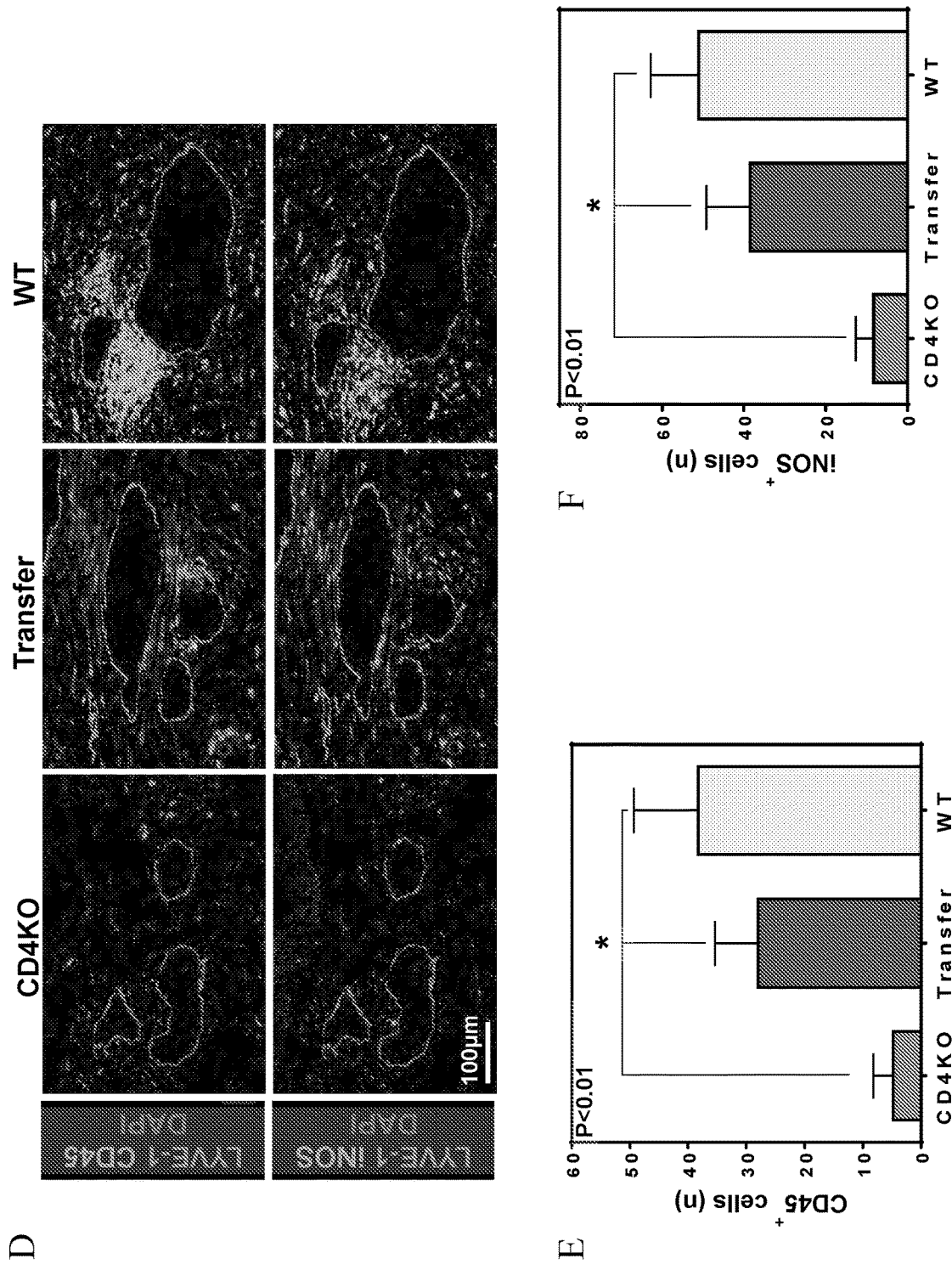

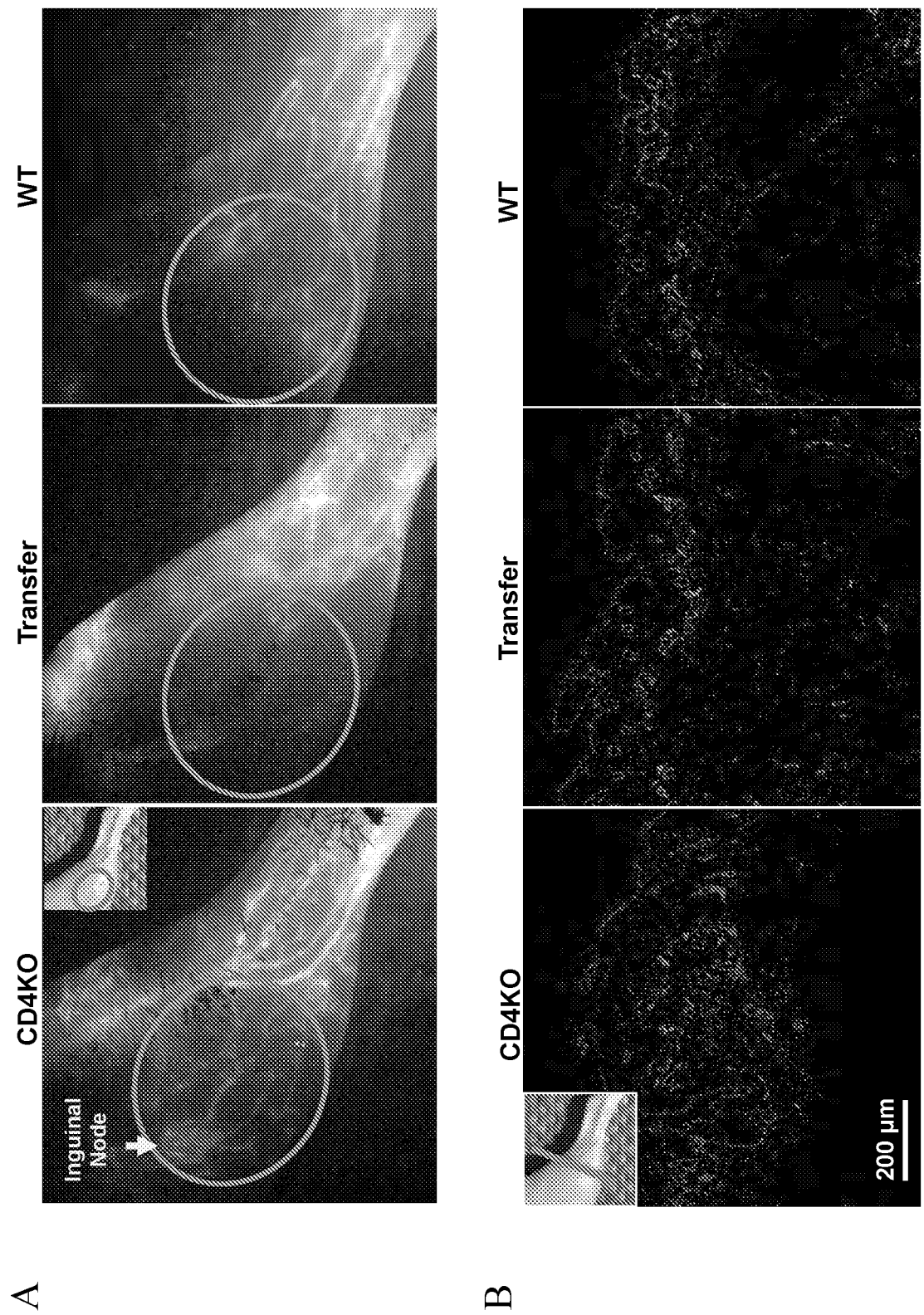

A

B

C

D

E

F

A

B

E

F

INHIBITION OF SPHINGOSINE 1-PHOSPHATE RECEPTOR FOR TREATMENT AND PREVENTION OF LYMPHEDEMA

CROSS-REFERENCE TO RELATED APPLICATIONS

This application is the National Stage of International Application No. PCT/US2017/047291, filed on Aug. 17, 2017, and claims the benefit of priority of U.S. Provisional Patent Application No. 62/376,496, filed on Aug. 18, 2016, the entire contents of both of which are incorporated by reference.

STATEMENT OF GOVERNMENT SUPPORT

This invention was made with government support under grant numbers HL111130 and CA008748, awarded by the National Institutes of Health. The government has certain rights in the invention.

COPYRIGHT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

INCORPORATION BY REFERENCE

For countries that permit incorporation by reference, all of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

BACKGROUND

Lymphedema is a chronic debilitating disease, characterized by fibrosis, chronic inflammation, and adipose deposition in the affected extremity. In the United States and Western countries, lymphedema occurs most frequently as a complication of cancer treatment. In this setting, lymphedema occurs as a result of iatrogenic injury to the lymphatic system, most commonly after lymph node dissection, but also as a result of wide skin excisions and adjuvant therapy with radiation. Purushotham et al., *J. Clin. Oncol.* 23:4312-4321 (2005); Szuba et al., *Cancer* 95:2260-2267 (2002); Tsai et al., *Ann. Surg. Oncol.* 16:1959-72 (2009). Because lymph nodes are located at intersections of the limbs with the trunk, disruption of lymphatic flow results in pooling of interstitial fluid and disturbances in immune function. Baird et al., *Am. J. Trop. Med. Hyg.* 66:163 (2002); Sugaya et al., *J. Invest. Dermatol.* 132:667 (2012). It is estimated that as many as 1 in 3 patients who undergo lymph node dissection will go on to develop lymphedema, and conservative estimates suggest that as many as 50,000 new patients are diagnosed annually. DiSipio et al., *Lancet Oncol.* 14:500-515 (2013); Petrek et al., *Cancer* 83:2776-2781 (1998).

Due to the key role of surgery and adjuvant radiotherapy in the treatment of most solid tumors, lymphedema is very common, afflicting an estimated 6 million cancer survivors in the United States alone. Rockson et al., *Ann. NY Acad. Sci.* 1131:147 (2008); Purushotham et al., *J. Clin. Oncol.* 23:4312 (2005); Szuba et al., *Cancer* 95:2260 (2002); Tsai et al., *Ann. Surg. Oncol.* 16:1959 (2009). Because lymphedema is a life-long disease with no cure, the number of affected individuals is increasing annually with current estimates of over 200 million people world-wide. It is likely that this number will continue to increase in the future since the development of lymphedema is nearly linearly related with cancer survivorship, and because the prevalence of known risk factors for lymphedema, such as obesity and radiation, is rising. Erickson et al., *J. Natl. Cancer Inst.* 93:96-111 (2001).

Lymphedema is disfiguring and debilitating; patients have chronic swelling of the affected extremity, chronic infections, limited mobility, a decreased quality of life, and in some cases, secondary malignancies. Bicego et al., *Phys. Ther.* 86:1398 (2006); Hayes et al., *Cancer* 118:2237-2249 (2012). In addition, once lymphedema develops, it is usually progressive. Despite the fact that lymphedema is common and highly morbid, there is currently no cure, and treatment is palliative with a goal of preventing disease progression rather than restoration of lymphatic function. Velanovich et al., *Am. J. Surg.* 177:184-187 (1999); Beaulac et al., *Arch. Surg.* 137; 1253-1257 (2002). As a result, patients are required to wear tight, uncomfortable garments for the rest of their lives, in an effort to prevent lymphatic fluid buildup in the affected extremity, and to undergo intense and time consuming physical therapy treatments. Koul et al., *Int. J. Radiat. Oncol. Biol. Phys.,* 67:841-846 (2007). In addition, despite on-going chronic care, some patients still have severe progression of their disease with increasing swelling and frequent infections in the lymphedematous limb. Currently there is no known pharmacologic therapy that can halt progression or promote resolution of lymphedema. Cormier et al., *Ann. Surg. Oncol.* 19:642-651 (2012). Development of targeted treatments for lymphedema is therefore an important goal and is an unmet biomedical need.

Recent studies have shown that fibrosis is not only a clinical hallmark of lymphedema, but also a key pathologic regulator of the disease. Cheville et al., *Semin. Radiat. Oncol.* 13:214-225 (2003); Mihara et al., *PLoS One* 7:e41126 (2012); Rasmussen et al., *Curr. Opin. Biotechnol.* 20:74-82 (2009). Inhibition of fibrotic responses preserves the capacity of the lymphatic system to transport interstitial fluid and inflammatory cells. Several lines of evidence suggest that $CD4^+$ T cells play a central role in the pathology of lymphedema. For example, Tekola et al. recently highlighted the association between HLA class II loci and podoconiosis, a tropical form of lymphedema, and concluded that this may be a T-cell mediated inflammatory disease. Tekola et al., *Trop. Med Int. Health* 13:1277 (2008). Our group has previously shown that the number of $CD4^+$ cells is increased in biopsy specimens harvested from patients with lymphedema. Avraham et al., *FASEB J.* 27:1114 (2013). More importantly, we have found that the number of tissue infiltrating $CD4^+$ cells has a linear positive correlation with the severity of lymphedema in these patients. Using mouse models of lymphedema, we have shown that in contrast to wild-type (WT) mice, animals lacking T cells in general (nude mice), or $CD4^+$ cells in particular, do not develop lymphedema following lymphatic injury. Avraham et al., *FASEB J.* 27:1114 (2013); Zampell et al., *PloS one* 7:e49940 (2012). Further, depletion of CD4+ cells with neutralizing antibodies prevents development of lymphedema. Avraham et al., *FASEB J.* 27:1114 (2013); Zampell et al., *PloS one* 7:e49940 (2012). This effect is specific to CD4+ cells since depletion of CD8+ cells or macrophages had either no effect or worsened lymphedematous skin changes. Zampell et al., *PloS one* 7:e49940 (2012). Finally, we have shown that Th2 differentiation of CD4+ cells is necessary for development of pathologic changes of lymphedema including fibrosis, impaired lymphangiogenesis, and impaired collecting lymphatic function. Avraham et al., *FASEB J.* 27:1114 (2013); Savetsky et al., *PloS one* 10:e012908 (2015).

However, while it is clear that CD4+ cells play a key role in the pathology of lymphedema, the mechanisms that regulate CD4+ activation, differentiation, and homing to lymphedematous tissues remains unknown. For example, it is unclear if naïve CD4+ cells require activation in skin draining lymph nodes in order to differentiate into effector cells that can infiltrate lymphedematous tissues. Additionally, the cellular signals that guide homing of effector CD4+ cells to lymphedematous tissues remain unknown. This gap in our knowledge is important, since identifying the mechanisms that regulate CD4+ cell activation and homing after lymphatic injury may identify novel treatment options for this disabling disease.

There are currently no pharmacologic therapies available for the treatment of lymphedema. Coumarin has been used in patients with lymphedema with modest success. Casley-Smith et al., *BMJ* 307:1037-1041 (1993); Casley-Smith et al., *N. Engl. J. Med.* 329:1158-1163 (1993); Casley-Smith et al., *Australas J. Dermatol.* 33:69-74 (1992); Loprinzi et al., *N. Engl. J. Med.* 340:346-350 (1999). However, widespread clinical application of this drug has been hampered by significant toxicity including liver failure and death. Loprinzi et al., *N. Engl. J. Med.* 340:346-350 (1999). Although highly effective, systemic depletion of CD4+ cells is not clinically viable due to unacceptable morbidity and systemic complications such as infections, cancer recurrence, and autoimmune disorders. Accordingly, there is a need in the art for novel treatments for lymphedema.

FTY720 is a small molecule agonist of the sphingosine 1-phosphate (S1P) receptor. It is derived from the antibiotic myriocin, and is a structural analogue of sphingosine. When phosphorylated by sphingosine kinase, FTY720 causes the internalization of S1P receptors, which blocks lymphocyte egress from the lymph nodes. Mandala et al., *Science* 296:346-349 (2002). FTY720 is FDA-approved under the brand name Gilenya® (fingolimod) for the treatment of patients with relapsing forms of multiple sclerosis (MS). We show here for the first time that blockade of T cell release from lymph nodes by downregulation of S1P using FTY720 prevented accumulation of activated T cells in skin, and potently inhibited development of lymphedema, showing that this approach can have clinical utility.

SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

In one aspect, the invention provides a method of treating or preventing lymphedema, the method comprising administering to a subject having lymphedema or susceptible to developing lymphedema a composition comprising an effective amount of an S1P receptor inhibitor. In another aspect, the invention provides a composition comprising an S1P receptor inhibitor for use in the treatment of lymphedema. In some instances, the S1P receptor inhibitor is selected from the group consisting of FTY720 (Fingolimod), ONO-4641 (Ceralifimod), RPC1063 (Ozanimod), ACT-128800 (Ponesimod), BAF312 (Siponimod), LT1009 (Sonepcizumab), AAL-R ((R)-2-amino-4-(4-heptyloxyphenyl)-2-methylbutanol), CS-0777 ((R)-1-(5-(3-amino-4-hydroxy-3-methylbutyl)-1-methyl-1H-pyrrol-2-yl)-4-(p-tolyl)butan-1-one), KRP-203 (2-amino-2-propanediol), RP-001 (N-[4-[5-[3-Cyano-4-(1-methylethoxy)phenyl]-1,2,4-oxadiazol-3-yl]-2, 3-dihydro-1H-iden-1-yl]-β-alanine), and Syl930. In a particular embodiment, the S1P receptor inhibitor is FTY720. In certain embodiments, the composition is administered orally or intravenously. In one embodiment, the subject of the treatment is a human subject. In one embodiment, the invention comprises administering a second active agent.

Lymphedema can arise from multiple causes, including abnormal development of the subject's lymphatic system or lymphatic injury. In one aspect, the lymphatic injury can be congenital. In other aspects, the lymphatic injury can result from surgery, trauma, radiation, chemotherapy, fibrosis of lymph tissue, infection (including viral, bacterial, and/or parasitic infection), or burns. The lymphatic injury can result from removal, ligation, or obstruction of lymph nodes or lymph vessels. In a particular aspect, the lymphatic injury can result from joint replacement surgery. In one embodiment, the composition comprising the S1P receptor inhibitor is administered prophylactically within about six weeks, preferably within about two weeks, of the lymphatic injury.

In some instances, the subject has undergone or is undergoing treatment for cancer. In prophylactic embodiments, the treatment with the S1P receptor inhibitor can commence before or concurrently with the cancer treatment. Cancer treatments can include surgery, chemotherapy, and radiation. In one embodiment, the cancer comprises a solid tumor.

In some instances, the subject is obese, overweight, or diabetic and has lymphatic dysfunction, swelling, or lymphedema from these conditions.

The methods and compositions of the invention can preferably be used to treat or prevent chronic lymphedema.

The invention also provides a method for inhibiting T cell infiltration into the skin of a subject, the method comprising administering to the subject an effective amount of an S1P receptor inhibitor.

BRIEF DESCRIPTION OF THE FIGURES

FIG. 1A shows representative dot plots of CD4+/CD3+ cells from spleen of CD4KO and adoptively transferred mice (Transfer). Note successful delivery of CD4+ cells in Transfer mice. FIG. 1B shows quantification of percentage CD4+/CD3+ cells in spleen. Transfer vs. CD4KO mice (*p<0.0001). FIG. 1C shows representative immunoflourescent images of TGF-β1+ cells (green) surrounding LYVE-1+ vessels (red). Nuclear DAPI is blue. Scale bar=5 μm. Note that adoptive transfer of CD4+ cells increases peri-lymphatic TGF-β1 expression. FIG. 1D shows quantification of perilymphatic TGF-β1+ cells per HPF of immunoflourescent images. CD4KO vs. Transfer and WT (*p<0.0001).

FIG. 2A shows a schematic diagram of the experimental protocol. FIG. 2B shows representative images of mouse tails 6 weeks after lymphatic ablation for CD4KO, Transfer, and WT groups. Note development of lymphedema in Transfer mice that is identical to WT mice. FIG. 2C shows quantification of percentage change in tail volumes (n=6-8 each). CD4KO (green) compared to WT (aqua) and Transfer (red) groups (*p<0.01). Note increased swelling (tail volume) in transfer and WT mice. FIG. 2D (upper panel) shows cross-sectional histology of mouse tails 6 weeks after lymphatic ablation for CD4KO, Transfer, and WT groups. Bracket surrounds skin and subcutaneous fibroadipose tissue. Note increased fibroadipose deposition in transfer and WT mice. FIG. 2D (lower panel) shows quantification of fibroadipose tissue thickness. CD4KO vs. Transfer and WT (*p<0.01). FIG. 2E shows quantification of decay adjusted uptake of $^{99m}$Tc over 90 min by sacral lymph nodes 6 weeks after tail lymphatic ablation. CD4 KO vs. Transfer and WT (*p<0.01). FIG. 2F (upper panels) shows representative immunoflorescent staining of collagen type I deposition (green) surrounding LYVE-1+ vessels (red) in tail sections of CD4KO, Transfer, and WT groups. Nuclear DAPI is blue. Scale bar=200 μm. Quantification of type I collagen deposition as a percentage of skin area is presented below the figure. Note increased fibrosis in Transfer and WT mice relative to CD4KO animal. FIG. 2F (middle panels) shows representative podoplanin (green) and α-SMA (red) staining of collecting lymphatic vessels from CD4KO, Transfer, and WT mouse hind limbs after popliteal dissection surgery. Nuclear DAPI is blue. Scale bar=40 μm. α-SMA thickness is quantified in the graph below. Notice the increased number of α-SMA cells around podoplanin-positive lymphatic endothelium of Transfer and WT mice, indicating fibrosis in these animals but not in the CD4KO group. FIG. 2F (lower panels) shows quantification of α-SMA thickness.

FIG. 3A shows a schematic representation of the experimental protocol for popliteal lymph node dissection (PLND) and adoptive transfer. FIG. 3B shows representative collector lymphatic pulsation frequency (packet frequency) graphs of CD4KO (green), Transfer (red), and WT (aqua) groups. Each spike represents a lymphatic pulsation as reflected by a change in ICG intensity. Note decreased pulsation in Transfer and WT mice relative to CD4KO animal. FIG. 3C shows quantification of packet frequency. CD4KO vs. Transfer and WT (*p<0.01). FIG. 3D shows representative images of mouse tails collected 6 weeks after lymphatic ablation in CD4KO mice, CD4KO mice adoptively transferred with WT CD4+ cells weekly, and WT mice. Immunoflorescent staining localizes capillary (LYVE-1+) lymphatic vessels (red) and CD45+ cells (green; upper panels) and iNOS+ cells (green; lower panels). Nuclear DAPI is blue. Scale bar=100 μm. FIG. 3E shows quantification of the number of pen-lymphatic CD45+ cells per HPF in tails of CD4KO, Transfer, and WT mice. CD4KO vs. Transfer and WT (*p<0.01). FIG. 3F shows quantification of the number of pen-lymphatic iNOS+ cells per HPF in tails of CD4KO, Transfer, and WT mice. CD4KO vs. Transfer and WT (*p<0.01).

FIG. 4A shows representative dot plots of CD4+ (upper panel) and CD45+ cells (lower panel) in tails at 6 weeks after lymphatic ablation from CD4KO, Transfer, and WT groups. FIG. 4B shows quantification of CD45+ and CD4/CD3/CD45+ cells from tails of CD4KO, Transfer, and WT groups. Adoptive transfer vs. CD4KO (*p<0.01).

FIG. 5A shows representative NIR images of hind limbs 4 weeks after popliteal surgeries for CD4KO, Transfer, WT, and iNOS KO groups. Red circle indicates anterolateral collaterals. Note absence of collaterals in Transfer and WT groups. FIG. 5B shows representative immunohistochemical images of LYVE-1+ vessels (red) in distal hind limbs of CD4KO, Adoptive transfer, and WT animals 4 weeks after surgeries. DAPI is blue. Scale bar=200 μm. FIG. 5C shows quantification of LYVE1+ vessels per HPF in tails. CD4KO vs. Adoptive transfer and WT (*p<0.01). CD4KO vs. Adoptive transfer and WT (*p<0.0001).

FIG. 6A shows a schematic diagram of the experimental protocol. FIG. 6B (left panel) shows representative dot plots of GFP+ cells from skin and subcutaneous tissues of adoptively transferred CD4KO mice after popliteal or sham surgeries. FIG. 6B (right panel) shows quantification of CD4+ cells from hind limb skin of adoptively transferred CD4KO mice after popliteal or sham surgeries. PLND vs. sham hind limbs (*p<0.01). FIG. 6C (upper panel) shows representative dot plots of Th1 (CCR5+/CXCR3+) cells from skin and subcutaneous tissues of adoptively transferred CD4KO mice after popliteal or sham surgeries. FIG. 6C (lower panel) shows representative dot plots of Th2 (CCR4+/CCR8+) cells from skin and subcutaneous tissues of adoptively transferred CD4KO mice after popliteal or sham surgeries. FIG. 6D shows quantification of Th1 (CCR5+/CXCR3+, left panel) and Th2 (CCR4+/CCR8+, right panel) cells from hind limbs of adoptively transferred CD4KO mice after popliteal or sham surgeries. PLND vs. sham hind limbs (*p<0.001). FIG. 6E (upper panels) shows representative immunoflourescent images of CD4+ (red)/IFN-γ+ (green) cells (putative Th1) in CD4KO and Transfer mice; WT not shown. Scale bar=50 μm. FIG. 6E (lower panels) shows representative immunoflourescent images of CD4+ (red)/IL4+ (green) (putative Th2) cells in CD4KO and Transfer mice; WT not shown. Scale bar=50 μm. FIG. 6F shows quantification of Th1 (CD4+/IFN-γ+ cells, left panel) and Th2 (CD4+/IL4+ cell, right panel) cells per HPF. CD4KO vs. Transfer and WT (*p<0.01). Note increased number of both Th1 and Th2 cells in Transfer and WT mice.

FIG. 7A shows quantification of skin homing receptors (CCR4, CCR10, CLA, CD11a), naive CD4+ cells marker (CCR7), and intestinal homing receptors (CCR9) in CD4+ cells harvested from the ipsilateral hind limb skin 6 or 24 hours after adoptive transfer in PLND or sham operated mice. FIG. 7B shows representative immunoflorescent images of tail cross-sections for lymphedema (left) and Sham (right) colocalizing LYVE-1+ vessels (red) and CCL17+ (green; upper panels) and CCL27+ cells (green; lower panels). Scale bar=30 μm. FIG. 7C shows representative immunoflourescent images of tail cross-sections for lymphedema (left) and Sham (right) colocalizing LYVE-1+ vessels (red) and E-selectin+ (white; upper panels), VCAM-1+ (white; middle panels), ICAM-1+ cells (white; lower panels). Scale bar=30 μm.

FIG. 9A shows a schematic representation of experimental protocol. FIG. 9B shows representative dot plots of CD4+ cells in inguinal lymph node and hind limb skin of PLND treated animals 6 hours (left panel) or 24 hours (right panel) after adoptive transfer of CD4+ cells. FIG. 9C shows quantification of CD4+ cells in the ipsilateral inguinal lymph node and skin for PLND treated animals 6 hours (left panel) and 24 hours (right panel) after adoptive transfer. Inguinal lymph node vs. hind limb skin *$p<0.0005$ at 6 hours and NS at 24 hours after adoptive transfer.

FIG. 10A shows representative dot plots of CD4+ cells in inguinal lymph node (upper panels), axillary lymph node (middle panels), or hind limb skin (lower panels) of Sham or PLND treated mice treated with or without FTY720. Cells were harvested 24 hours after adoptive transfer. FIG. 10B shows quantification of CD4+ cells in inguinal lymph node (left panel), axillary lymph node (middle panel), and hind limb skin (right panel) for Sham (yellow), PLND (green), and PLND+FTY720 (red) groups 24 hours after adoptive transfer of CD4+ cells. $P<0.05$ for Sham vs. PLND vs. PLND+FTY720. Note that FTY720 prevented release of CD4+ cells from the lymph node and decreased the number of these cells in hind limb skin. FIG. 10C shows representative images of mouse tails 6 weeks after lymphatic ablation and treatment with either vehicle control or FTY720. Note lack of swelling and fibrosis ("J" configuration) of FTY720 treated mouse tail. FIG. 10D shows quantification of percentage change in tail volumes of control and FTY720 treated mice (n=6-8 each). Note lack of swelling in FTY720 treated mice. FIG. 10E shows cross-sectional histology of mouse tails 6 weeks after lymphatic ablation for Control and FTY720 groups. Bracket surrounds skin and subcutaneous fibroadipose tissue. Note decreased fibroadipose tissue deposition in FTY720 treated mice. FIG. 10F shows quantification of fibroadipose tissue thickness in control vs. FTY720 treated mice.

FIG. 11A shows a schematic diagram of the experimental plan showing adoptive transfer of CD45.1+ dendritic cells to CD4KO or wild-type mice 2 weeks after PLND or sham surgery. FIG. 11B shows quantification of activated donor dendritic cells (CD45.1+, CD11c+, MHCII+; CD45.1+, CD11e+, CD86+) in hind limb skin of CD4KO PLND (green) and Sham (red) groups 6 hours or 24 hours after adoptive transfer. FIG. 11C shows quantification of activated donor dendritic cells (CD45.1+, CD11e+, MHCH+; CD45.1+, CD11c+, CD86+) in inguinal lymph node (green) and hind limb skin (red) of CD4KO mice treated with PLND 6 hours and 24 hours after adoptive transfer. FIG. 11D shows quantification of CD45.1+ cells in ipsilateral inguinal lymph node or hind limb skin of sham operated CD4KO mice (red) and PLND treated CD4KO (light green) or WT PLND (dark green) mice 6 hours and 24 hours after adoptive transfer. FIG. 11E shows quantification of CD4+ cells in lymph node (left panel) and skin (right panel) for WT (red) and CD28KO (green) mice 2 weeks after PLND. $P<0.05$ for CD28KO vs. WT PLND in skin. P=NS in lymph node. FIG. 11F shows quantification of skin homing receptors (CCR4, CCR10, CLA, CD11a), naive CD4+ cells marker (CCR7), intestinal homing receptors (CCR9), and Th2 differentiation markers (CCR8, CCR4) in CD4+ cells harvested from the ipsilateral hind limb skin collected 2 weeks after surgery on PLND treated WT or CD28KO mice.

DETAILED DESCRIPTION OF THE INVENTION

Figure 1:
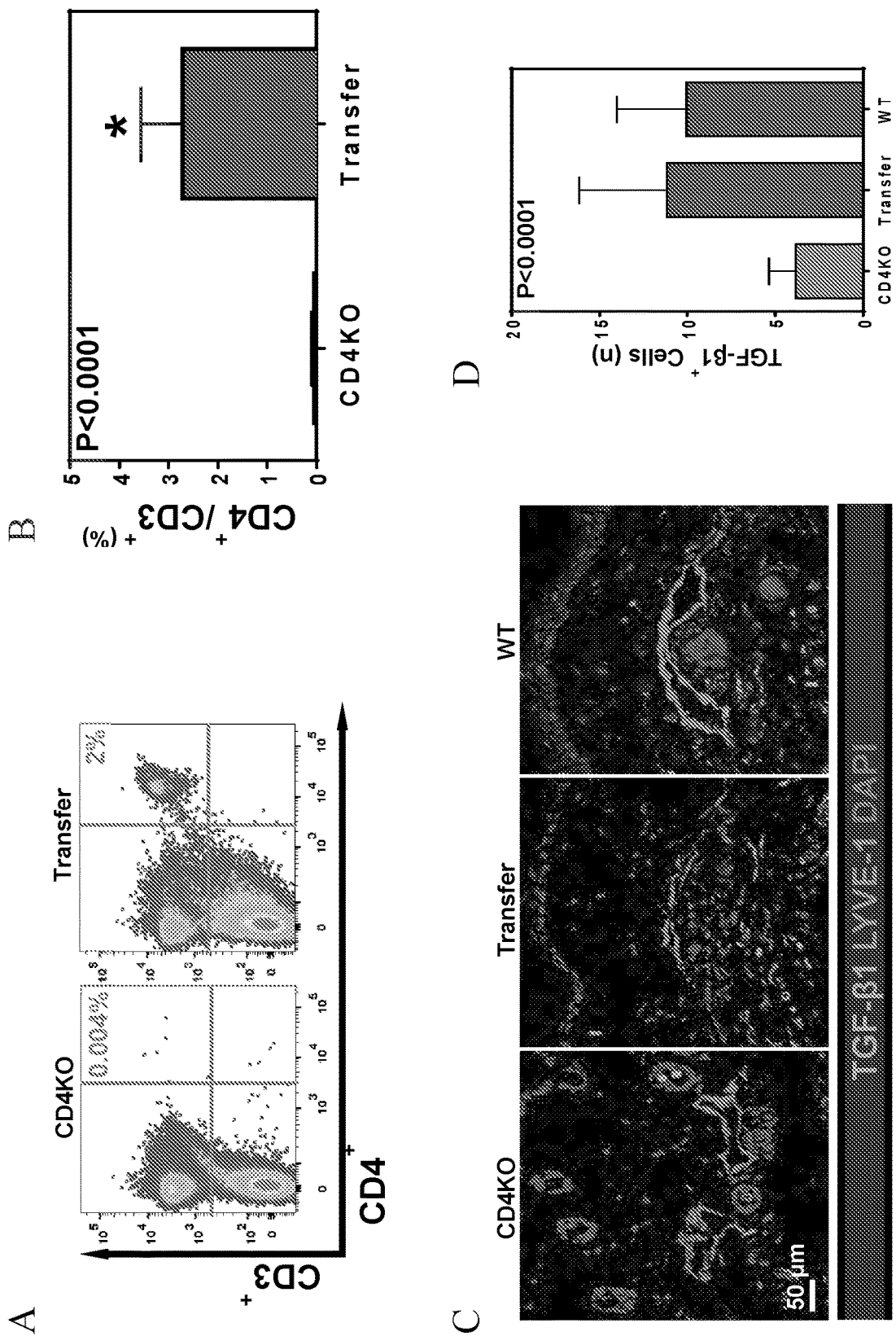
FIG. 1A-1D show that CD4+ cells are required for capillary and collecting vessel fibrosis.

Using several models of lymphedema and lymphatic injury we show that dendritic cells are activated in the sites of lymphatic injury and migrate to the skin-draining lymph nodes (located in proximity to the zone of lymphatic injury), where they activate peripheral CD4+ cells. We show that this process leads to the expression of cell surface receptors that enable homing of T effector cells to lymphedematous skin. Activated CD4+ cells orchestrate perilymphatic accumulation of inflammatory cells, deposition of extracellular matrix products, and proliferation of collecting lymphatic smooth muscle cell, and also inhibit formation of collateral lymphatics. These pathologic changes lead to impaired lymphatic function and pathological tissue changes of lymphedema. Our studies show that even a small number of naive CD4+ cells are sufficient to induce lymphedema after lymphatic injury. Therefore, it is likely that after lymphatic injury, activated CD4+ cells acquire the ability to home to lymphedematous tissues and proliferate sufficiently to orchestrate the pathologic responses of lymphedema. Thus, preventing the infiltration of CD4+ T cells in skin addresses the cause of these pathologic responses.

The present invention relates, in part, to the use of an SW receptor inhibitor, such as FTY 720, as a novel, safe, and effective treatment for lymphedema, especially chronic lymphedema. The present invention is based, in part, on the surprising discovery that administration of an SW receptor inhibitor prevents accumulation of activated T cells in the skin, and markedly improves symptoms of lymphedema, including swelling and fibrosis, when administered to mammalian subjects.

Accordingly, the present invention provides compositions and methods for treating or preventing lymphedema, and/or for producing a variety of other beneficial biological effects including, but not limited to: reduced tissue swelling, reduced lymphatic fluid stasis or "pooling," reduced tissue fibrosis, reduced tissue inflammation, reduced infiltration of leukocytes, reduced infiltration of macrophages, reduced infiltration of naïve and differentiated T-cells, particularly in the skin, reduced collagen deposition and/or scar formation, and/or improved or increased lymphatic function.

Unless defined otherwise, all technical and scientific terms used herein have the same meaning as commonly understood by one of ordinary skill in the art to which this invention is related. For example, *The Dictionary of Cell and Molecular Biology* (5th ed. J. M. Lackie ed., 2013), the *Oxford Dictionary of Biochemistry and Molecular Biology* (2d ed. R. Cammack et al. eds., 2008), and *The Concise Dictionary of Biomedicine and Molecular Biology* (2d ed.

P-S. Juo, 2002) can provide one of skill with general definitions of some terms used herein.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Systéme International de Unites (SI) accepted form. Numeric ranges are inclusive of the numbers defining the range. Where a numeric term is preceded by "about," the term includes the stated number and values ±10% of the stated number. The headings provided herein are not limitations of the various aspects or embodiments of the invention, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are included.

The term "lymphedema," as used herein, includes lymphatic tissue fibrosis and lymphatic injury, obstruction, and/or dysfunction. Lymphedema can include acute lymphedema, chronic lymphedema, congenital lymphedema, post-operative lymphedema, and gradual-onset lymphedema. Symptoms of lymphedema can include swelling, fullness, or puffiness of tissues, inflammation, fibrosis, heaviness, pain, decreased range of motion, aching, recurring infections, skin thickening, and/or discomfort.

An "active agent" is an agent which itself has biological activity, or which is a precursor or prodrug that is converted in the body to an agent having biological activity. Active agents useful in the methods of the invention include S1P receptor inhibitors.

An "S1P receptor inhibitor" is an active agent that agonizes or antagonizes the activity of an S1P receptor. A preferred S1P receptor inhibitor for treating or preventing lymphedema is FTY720. As used herein, the term "FTY720" refers to 2-amino-2-[2-(4-octylphenyl)ethyl]propane-1,3-diol and its salts, and further includes the phosphorylated form, 2-amino-2-[2-(4-octylphenyl)ethyl] propane-1,3-diol, mono dihydrogen phosphate ester (FTY720P). Other examples of S1P receptor inhibitors include ONO-4641 (Ceralifimod), RPC1063 (Ozanimod), ACT-128800 (Ponesimod), BAF312 (Siponimod), LT1009 (Sonepcizumab), AAL-R ((R)-2-amino-4-(4-heptyloxyphenyl)-2-methylbutanol), CS-0777 ((R)-1-(5-(3-amino-4-hydroxy-3-methylbutyl)-1-methyl-1H-pyrrol-2-yl)-4-(p-tolyl)butan-1-one), KRP-203 (2-amino-2-propanediol), RP-001 (N-[4-[5-[3-Cyano-4-(1-methylethoxy)phenyl]-1,2,4-oxadiazol-3-yl]-2,3-dihydro-1H-iden-1-yl]-β-alanine), and Syl930 (Jin et al. *Biochem. Pharmacol.* 90:50-61 (2014). Additional examples of S1P receptor inhibitors include AKP-11 (Samuvel et al., *PLoS One* 10:e0141781 (2015), CS 2100 (Nakamura et al., *Bioorg. Med. Chem. Lett.* 22:1788-1792 (2012)), CYM 5442 (Gonzalez-Cabrera et al., *Mol. Pharmacol.* 74:1308-1318 (2008)), CYM 50260 (Guerrero et al., *Bioorg. Med. Chem. Lett.* 22:537-542 (2012)), CYM 50308 (Urbano et al., *Bioorg. Med. Chem. Lett.* 21:6739-6745 (2011)), JTE 013 (Parrill et al., *Semin. Cell Dev. Biol.* 15:467-476 (2004)), SEW 2871 (Hale et al., *J. Med. Chem.* 47:6662-6665 (2004)), TC-SP 14 (Clemens et al., *Bioorg. Med. Chem. Lett.* 15:3568-3572 (2005), VPC23019 (Davis, et al., *J. Biol. Chem.* 280:9833-9841 (2005), W146 (Sanna et al., *Nat. Chem. Biol.* 2:434-441 (2006)). The term "S1P receptor inhibitor" includes phosphorylated forms and pharmaceutically acceptable salts of the disclosed compounds. Further S1P receptor inhibitors are discussed, for example, in Guerrero et al., *Expert Opin. Ther. Pat.* 26:455-470 (2016).

The terms "inhibit," "block," and "suppress" are used interchangeably and refer to any statistically significant decrease in biological activity, including full blocking of the activity.

By "subject" or "individual" or "patient" is meant any subject, preferably a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, and so on.

In some embodiments the subject may have or may have had cancer, for example, a cancer comprising a solid tumor. In some embodiments the subject may have or may have had breast cancer or a cancer affecting male or female reproductive organs, cutaneous system, musculoskeletal system, soft tissues of the extremities or trunk, urinary system, or the head and neck. In some embodiments, the subject may have undergone lymph node dissection. In some embodiments, the subject has received treatment for cancer, and the lymphedema or lymphatic injury is associated with the cancer treatment or diagnosis. For example, the subject may be receiving or may have received chemotherapy or radiation therapy for cancer treatment or other indications, or may have had one or more lymph nodes surgically removed in the course of cancer treatment or diagnosis.

In some embodiments the subject may have sustained a lymphatic injury (for example as the result of removal, ligation or obstruction of lymph nodes or lymph vessels, or fibrosis of lymph tissue), or the subject may be obese or have or had an infection that leads to lymphedema. In some embodiments the infection may be a skin infection or a history of skin infection(s) that are related to lymphedema or lymphatic injury. In some embodiments the infection may be a parasitic infection that obstructs lymphatic flow or injures the lymphatic system. In some embodiments the subject may have sustained lymphatic injury from joint replacement, trauma, burns, radiation, or chemotherapy.

Terms such as "treating" or "treatment" or "to treat" or "alleviating" or "to alleviate" refer to therapeutic measures that cure, slow down, lessen symptoms of, and/or halt progression of a diagnosed pathological condition or disorder. Thus, those in need of treatment include those already with the disorder. In certain embodiments, a subject is successfully "treated" for a disease or disorder according to the methods provided herein if the patient shows, e.g., total, partial, or transient alleviation or elimination of symptoms associated with the disease or disorder. For example, "treating lymphedema" can include, but is not limited to, decreasing swelling, decreasing inflammation, decreasing fibrosis, decreasing pain, increasing range of motion, decreasing heaviness, decreasing tightness, decreasing skin thickening, improving subjective symptoms, and/or improving lymphatic function.

"Prevent" or "prevention" refers to prophylactic or preventative measures that prevent and/or slow the development of a targeted pathologic condition or disorder. Thus, those in need of prevention include those at risk of or susceptible to developing the disorder. Subjects that are at risk of or susceptible to developing lymphedema include, but are not limited to, cancer patients undergoing radiation therapy, chemotherapy, and/or surgical lymph node dissection. Subjects having acute lymphedema can be at risk for developing chronic lymphedema. In certain embodiments, a disease or disorder is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

In a prophylactic context, the pharmaceutical composition of the invention can be administered at any time before or after an event, for example, radiation therapy, chemotherapy, or surgical lymph node dissection, which places a subject at risk of or susceptible to lymphatic injury and/or developing lymphedema. In some aspects, the pharmaceutical composition is administered prophylactically up to about one week before the event, such as 1, 2, 3, 4, 5, 6, or 7 days before the event. In some instances, the pharmaceutical composition is administered prophylactically on the same day as the event. In some embodiments, the pharmaceutical composition is administered prophylactically within 3 years of the event, for example, within about 1, 2, 3, 4, 5, or 6 days, or within about 1, 2, 3, 4, 5, 6, 7, 8, 9, 10, 11, or 12 weeks, or within about 3, 6, 12, 18, 24, 30, or 36 months.

In some embodiments the treatment and/or prevention methods described herein may be performed in combination with one or more additional lymphedema treatment and/or prevention methods known in the art, for example, treatment methods involving the administration of other therapeutic agents and/or treatment methods involving surgery, massage, compression therapy, fluid drainage therapy, acupuncture, laser, or any other suitable treatment methods.

In particular, one aspect of the invention can comprise administering a second active agent, in addition to the S1P receptor inhibitor. For example, the second active agent can include an anti-T cell agent, an anti-TGF-β1 agent, or an anti-angiotensin agent. In a particular embodiment, the second active agent can be selected from the group consisting of tacrolimus, teriflunomide, leflunomide, cyclosporine, pimecrolimus, denileukin diftitox, Basiliximab, pirfenidone, captopril, zofenopril, enalapril, lisinopril, ramipril, quinapril, perindopril, benazepril, imidapril, trandolapril, cilazapril, fosinopril, losartan, irbesartan, olmesartan, candesartan, telmisartan, valsartan, and fimasartan.

The term "pharmaceutical composition" refers to a preparation that is in such form as to permit the biological activity of the active ingredient to be effective, and which contains no additional components that are unacceptably toxic to a subject to which the composition would be administered. Pharmaceutical compositions can be in numerous dosage forms, for example, tablet, capsule, liquid, solution, softgel, suspension, emulsion, syrup, elixir, tincture, film, powder, hydrogel, ointment, paste, cream, lotion, gel, mousse, foam, lacquer, spray, aerosol, inhaler, nebulizer, ophthalmic drops, patch, suppository, and/or enema. Pharmaceutical compositions typically comprise a pharmaceutically acceptable carrier, and can comprise one or more of a buffer (e.g. acetate, phosphate or citrate buffer), a surfactant (e.g. polysorbate), a stabilizing agent (e.g. human albumin), a preservative (e.g. benzyl alcohol), a penetration enhancer, an absorption promoter to enhance bioavailability and/or other conventional solubilizing or dispersing agents. Choice of dosage form and excipients depends upon the active agent to be delivered and the disease or disorder to be treated or prevented, and is routine to one of ordinary skill in the art.

"Systemic administration" means that a pharmaceutical composition is administered such that the active agent enters the circulatory system, for example, via enteral, parenteral, inhalational, or transdermal routes. Enteral routes of administration involve the gastrointestinal tract and include, without limitation, oral, sublingual, buccal, and rectal delivery. Parenteral routes of administration involve routes other than the gastrointestinal tract and include, without limitation, intravenous, intramuscular, intraperitoneal, intrathecal, and subcutaneous. "Local administration" means that a pharmaceutical composition is administered directly to where its action is desired (e.g., at or near the site of the injury or symptoms). Local routes of administration include, without limitation, topical, inhalational, subcutaneous, ophthalmic, and otic. It is within the purview of one of ordinary skill in the art to formulate pharmaceutical compositions that are suitable for their intended route of administration.

An "effective amount" of a composition as disclosed herein is an amount sufficient to carry out a specifically stated purpose. An "effective amount" can be determined empirically and in a routine manner, in relation to the stated purpose, route of administration, and dosage form.

In some embodiments, administration of the S1P receptor inhibitor can comprise systemic administration, at any suitable dose and/or according to any suitable dosing regimen, as determined by one of skill in the art. For example, in some embodiments, FTY720 is administered systemically to the subject at a daily dose of about 0.1 mg to about 5 mg. More particularly, FTY720 can be administered to the subject at a daily dose of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.25, 3.5, 3.75, 4.0, 4.25, 4.5, 4.75, or 5.0 mg. In other embodiments, FTY720 can be administered to the subject at a daily dose of about 0.001 to about 2.5 mg/kg. More particularly, FTY720 can be administered to the subject at a daily dose of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, or 2.5 mg/kg.

The S1P receptor inhibitor can be administered according to any suitable dosing regimen, for example, where the daily dose is divided into two or more separate doses. It is within the skill of the ordinary artisan to determine a dosing schedule and duration for administration. In some embodiments, the pharmaceutical composition is administered orally at least once a day or at least twice a day. In some embodiments, the pharmaceutical composition is administered intravenously at least once a day or at least twice a day. In some embodiments, the pharmaceutical composition is administered subcutaneously at least once a day or at least twice a day.

In embodiments in which more than one active agent is administered, the agents can be administered together (for example, in the same formulation and/or at the same time), or separately (for example, in different formulations and/or at different times). In some such embodiments, the agents are administered systemically. In some such embodiments, the agents are administered locally. In some such embodiments, one (or more) agent is administered systemically and one (or more) agent is administered locally, for example, topically.

Embodiments of the present disclosure can be further defined by reference to the following non-limiting examples. It will be apparent to those skilled in the art that many modifications, both to materials and methods, can be practiced without departing from the scope of the present disclosure.

EXAMPLES

Example 1

Figure 2:
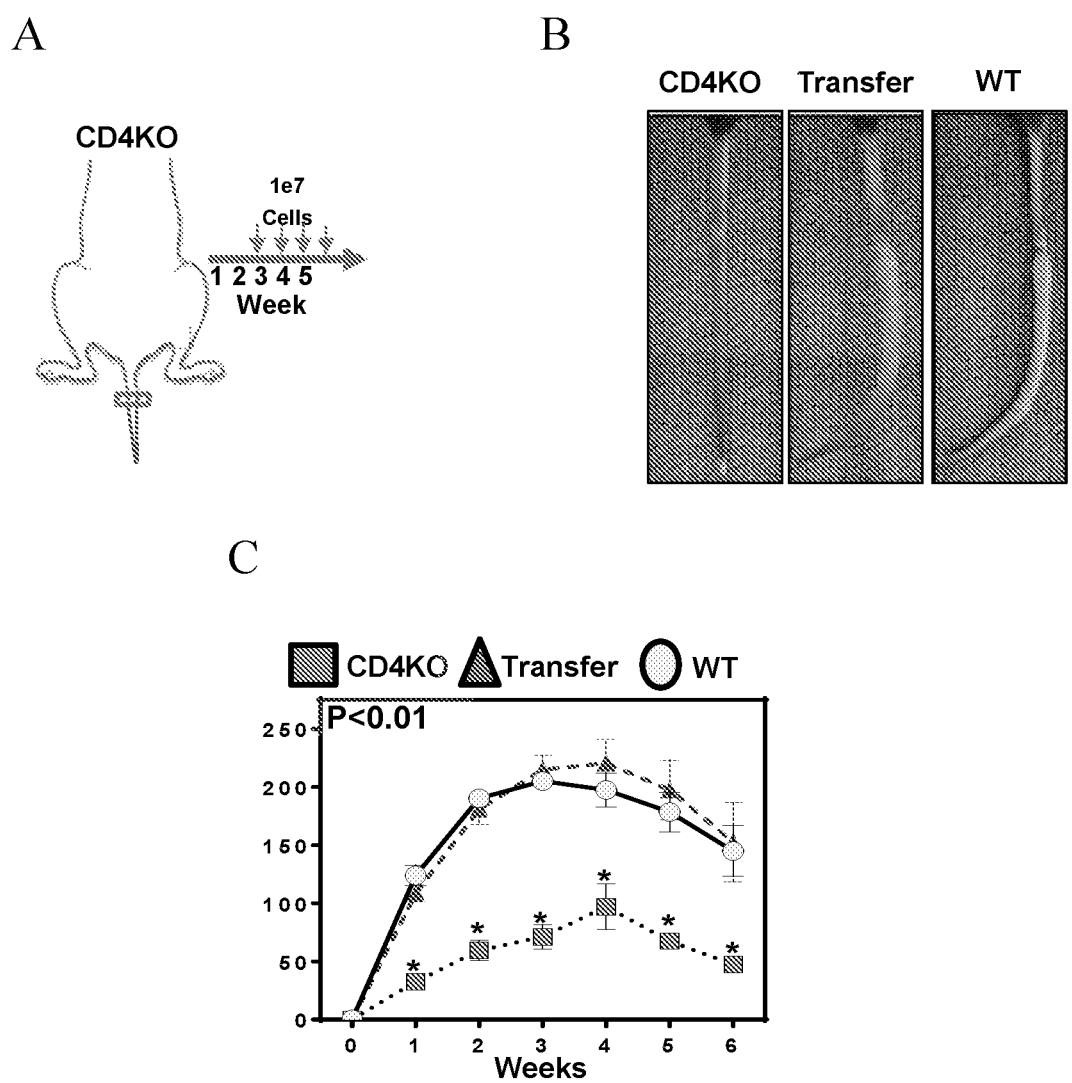
FIG. 2A-2F show that adoptive transfer of CD4+ cells to CD4KO mice after lymphatic injury results in development of lymphedema.
Figure 2:
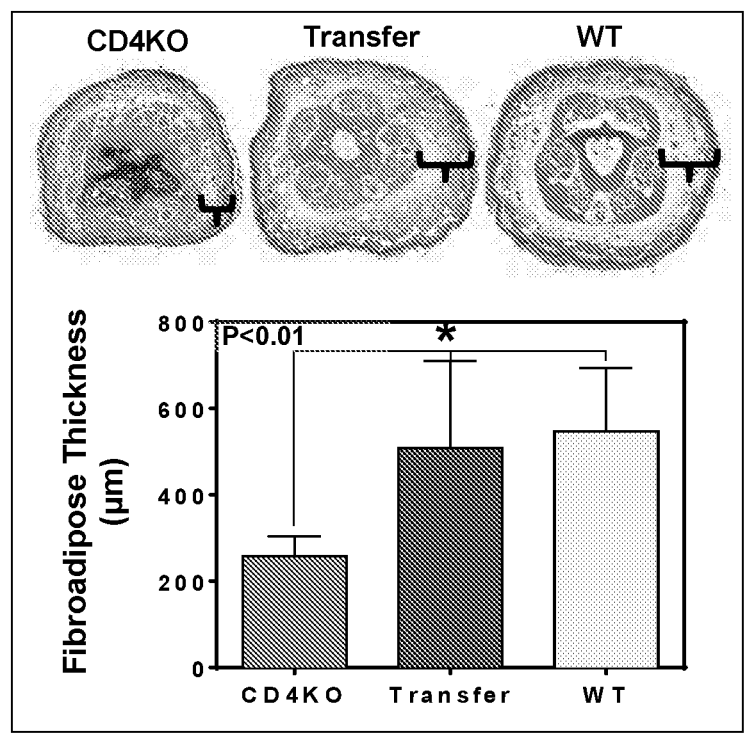
Figure 2:
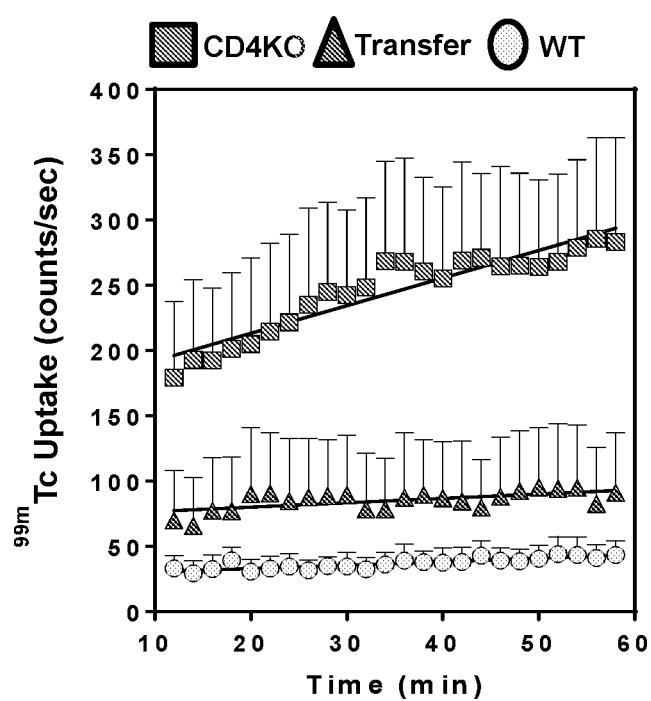
Figure 2:
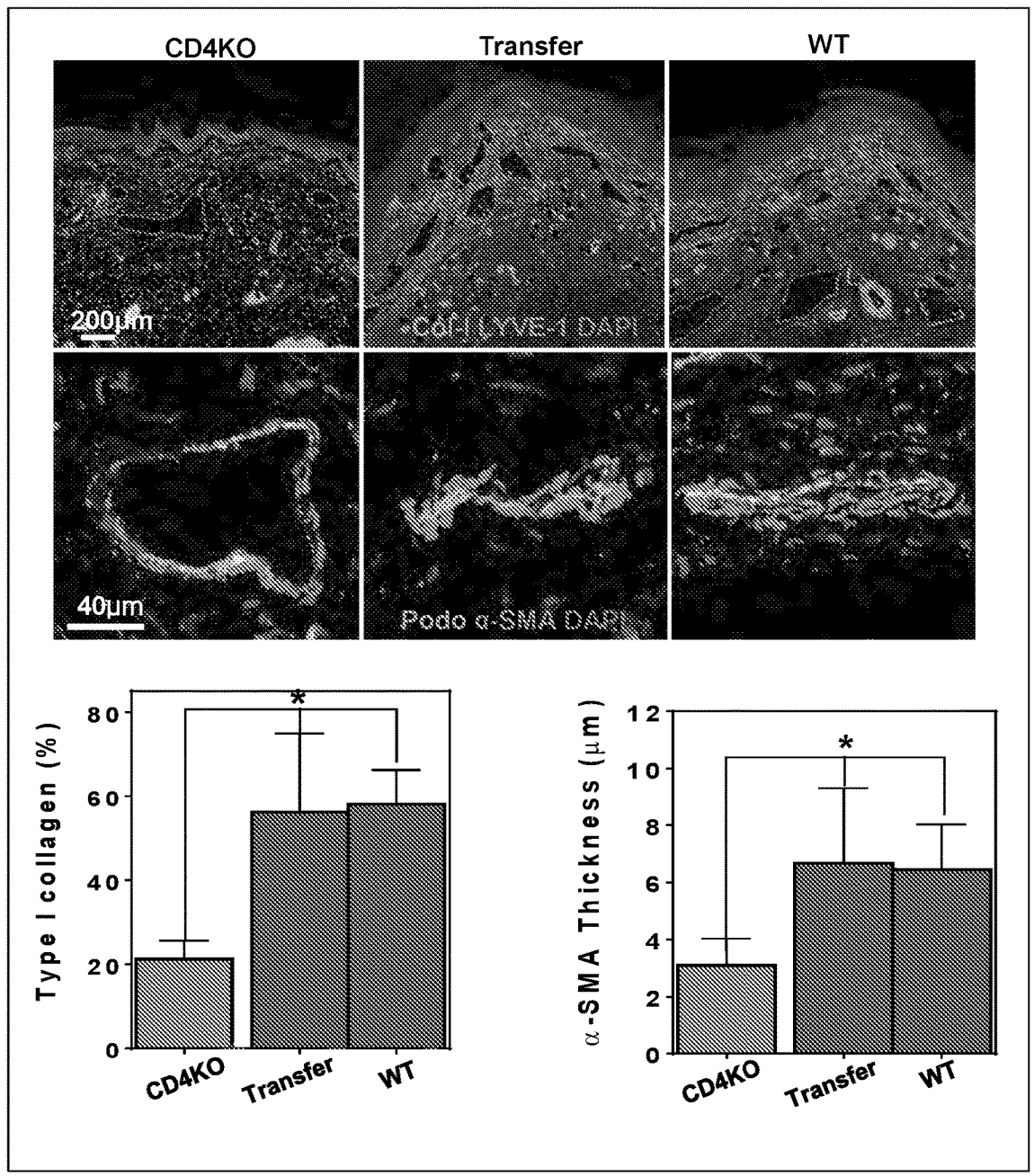

Adoptive Transfer of CD4+ Cells after Lymphatic Injury Results in Development of Lymphedema We sought to determine whether adoptive transfer of naïve CD4$^+$ cells to CD4KO mice subjected to lymphatic injury was sufficient to induce lymphedema. CD4KO mice underwent tail lymphatic ablation; beginning two weeks after injury, and then weekly thereafter for 4 weeks, the animals were adoptively transferred with $1 \times 10^7$ naïve splenic CD4$^+$ cells harvested from uninjured donor WT mice. We confirmed successful CD4$^+$ cell isolation and naïve status after expansion, as well as successful delivery of CD4$^+$ cells to CD4KO mice, using flow cytometry on splenic single cell suspensions (FIG. 1A). Adoptive transfer of WT CD4$^+$ cells to CD4KO mice resulted in development of phenotypic features of lymphedema including swelling, fibrosis (curvature) of the tail, and histological changes that were nearly identical to WT mice (FIG. 2A-2C). Likewise, adoptively transferred CD4KO mice had markedly impaired lymphatic transport function with a significant decrease in the decay adjusted uptake of Tc$^{99}$ in the sacral lymph nodes after distal tail injection (FIG. 2D).

Because fibrosis is a clinical hallmark of lymphedema, we sought to determine whether adoptively transferred CD4$^+$ cells were sufficient to induce extracellular matrix collagen I deposition after lymphatic injury. Indeed, immunohistochemical analysis of tail tissues harvested from WT and CD4KO mice adoptively transferred with CD4$^+$ cells demonstrated a marked accumulation of type I collagen in the dermis and subcutaneous tissues (FIG. 3E upper panel; FIG. 1C). Collagen bundles virtually encased dermal lymphatic capillaries in these animals. In contrast, analysis of tail tissues from control CD4KO mice demonstrated sparse staining for type I collagen overall, and virtually no collagen fibers around capillary lymphatics.

Figure 3:
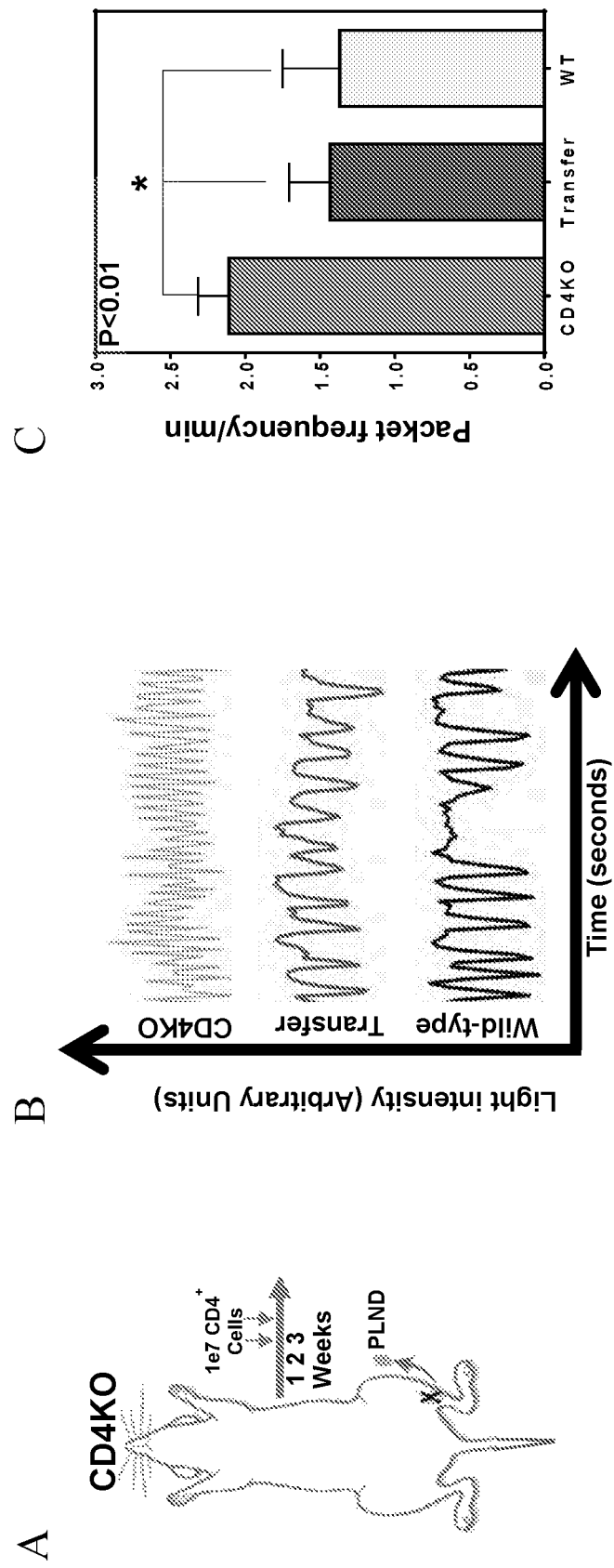
FIG. 3A-3F show that adoptively transferred CD4+ cells regulate lymphatic pumping and perilymphatic inflammation after lymphatic injury.

Previous studies have shown that lymphedema results in progressive accumulation of alpha smooth muscle actin (α-SMA) cells around collecting lymphatics. Mihara et al., *PloS one* 7:e41126 (2012). In fact, in late stages of the disease, this accumulation of α-SMA cells is thought to result in the eventual obliteration of collecting lymphatics. We therefore analyzed the main hind limb collecting lymphatics of WT and CD4KO mice with or without adoptive transfer. We identified these lymphatic channels using anatomical landmarks as well as co-localization of podoplanin and α-SMA (FIG. 3E lower panel). Grossly, we noted that lymphatic collectors in WT and adoptively transferred CD4KO mice had a more collapsed appearance as compared with collecting lymphatics in control CD4KO animals. In addition, consistent with clinical studies, we found that both WT and adoptively transferred CD4KO mice had a marked accumulation (more than 2-fold increase) in the number of perilymphatic α-SMA positive cells. TGF-β1 is a key profibrotic cytokine and our group has noted its importance in the phathophysiology of lymphedema. Avraham et al., *Am. J. Pathol.* 177:3202 (2010). Both WT and adoptively transferred CD4KO mice had a more than 2-fold increase in the number of TGF-β1$^+$ cells as compared with control CD4KO mice (FIG. 1B, 1D).

Example 2

CD4+ Cells Regulate Lymphatic Pumping and Perilymphatic Inflammation after Lymphatic Injury Previous experimental studies have shown that PLND results in physiological changes and impaired pumping in collecting lymphatics. Kwon et al., *PloS one* 9:e106034 (2014). Similarly, clinical studies have shown that patients with breast cancer related lymphedema have impaired lymphatic pumping capacity as compared to normal controls. Modi et al., *J. Physiol.* 583:271 (2007). However, despite that it is clear that lymphatic pumping is altered in lymphedema and may contribute to the pathology of this disease, the cellular mechanisms that regulate this response remain unknown. In these experiments, CD4KO mice underwent PLND, were allowed to recover for 1 week, and then were either injected with PBS (controls) or adoptively transferred with $1 \times 10^7$ naïve CD4$^+$ cells harvested from wild-type mice once per week for 3 weeks (FIG. 3A). Analysis of control CD4KO mouse lymphatics 4 weeks after PLND demonstrated rapid lymphatic pumping (packet frequency; FIG. 3B). In contrast, adoptively transferred CD4KO mice and WT controls demonstrated a marked decrease in hind limb collecting lymphatic pumping frequency (>1.5-fold decrease in packet frequency; $p<0.01$).

Figure 4:
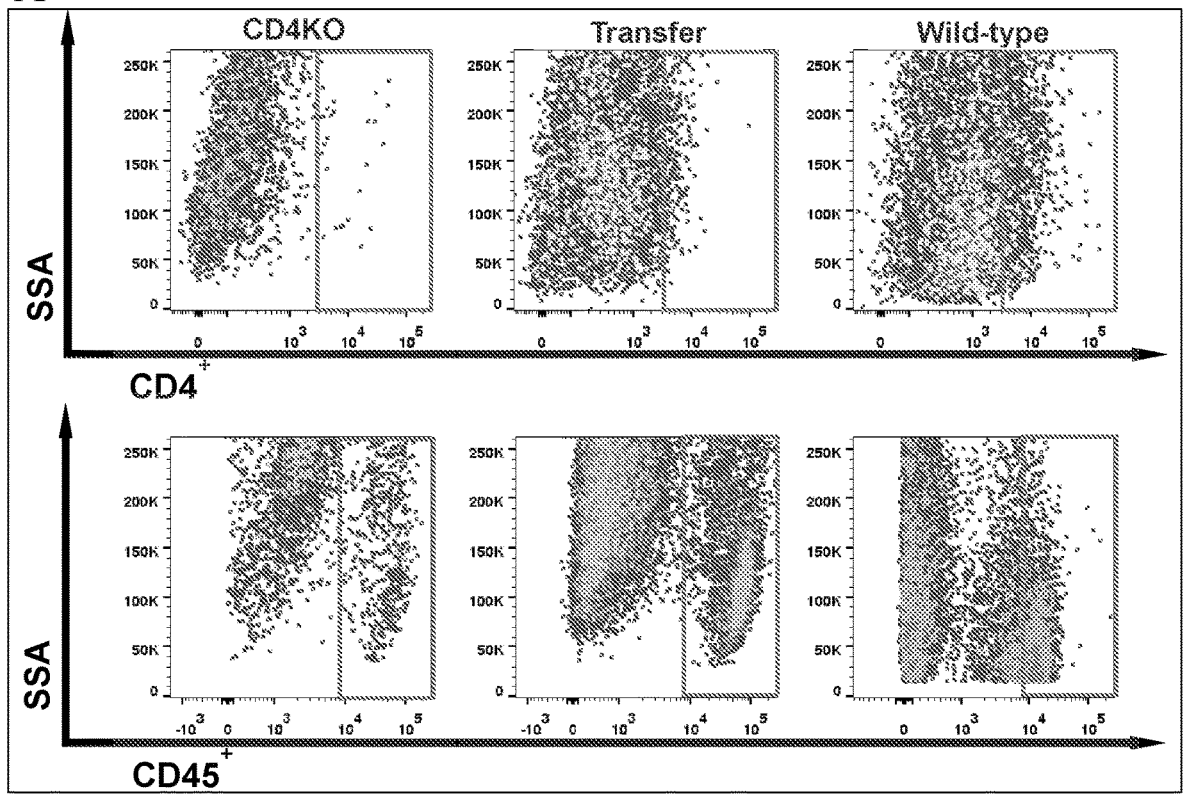
FIG. 4A-4B show that adoptive transfer of CD4+ cells results in increased local inflammation in areas of lymphatic injury.
Figure 4:
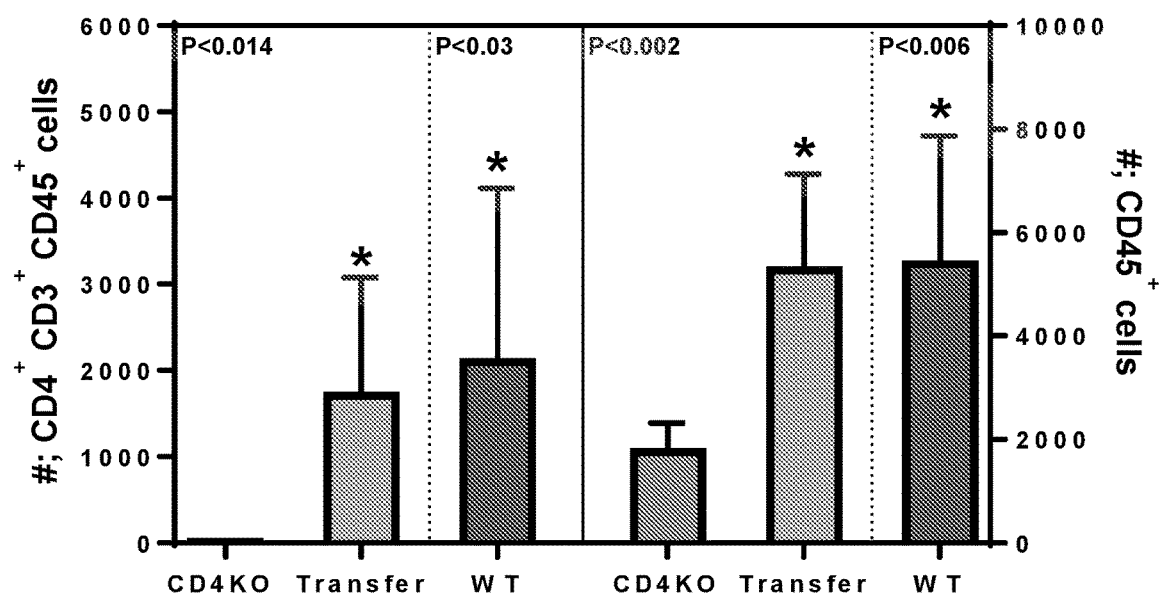

Previous studies have shown that inflammatory stimuli decrease lymphatic contractility, at least in part, by increased expression by inflammatory cells of induced nitric oxide synthase (iNOS), with resultant disruption of endogenous nitric oxide (NO) gradients that are ordinarily regulated by endothelial derived nitric oxide synthase (eNOS). Ferguson et al., *Microvasc. Res.* 47:308 (1994); Leak et al., *Biochem. Biophys. Res. Comm.* 217:96 (1995); Gashev et al., *J. Physiol.* 540:1023 (2002); Liao et al., *Proc. Natl. Acad. Sci. USA* 108:18784 (2011). Consistent with these findings, flow cytometry of distal tail tissues demonstrated a marked increase in the number of skin inflammatory cells 6 weeks after lymphatic ablation in adoptively transferred and WT groups, as compared with CD4KO mice (FIG. 4A-4B). Consequently, we next sought to determine whether adoptive transfer of CD4$^+$ cells leads to changes in perilymphatic iNOS expression after lymphatic injury. Indeed, analysis of tail tissue sections co-localizing lymphatic vessels (LYVE-1$^+$), inflammatory cells (CD45$^+$) and iNOS demonstrated a marked perilymphatic accumulation of iNOS$^+$ inflammatory cells in adoptively transferred CD4KO and WT, but not control, CD4KO mice (FIG. 3C-3E). In addition, consistent with increased expression of iNOS, we noted that the lymphatic vessels in Transfer and WT mice were significantly more dilated than in CD4KO mice.

Example 3

Figure 5:
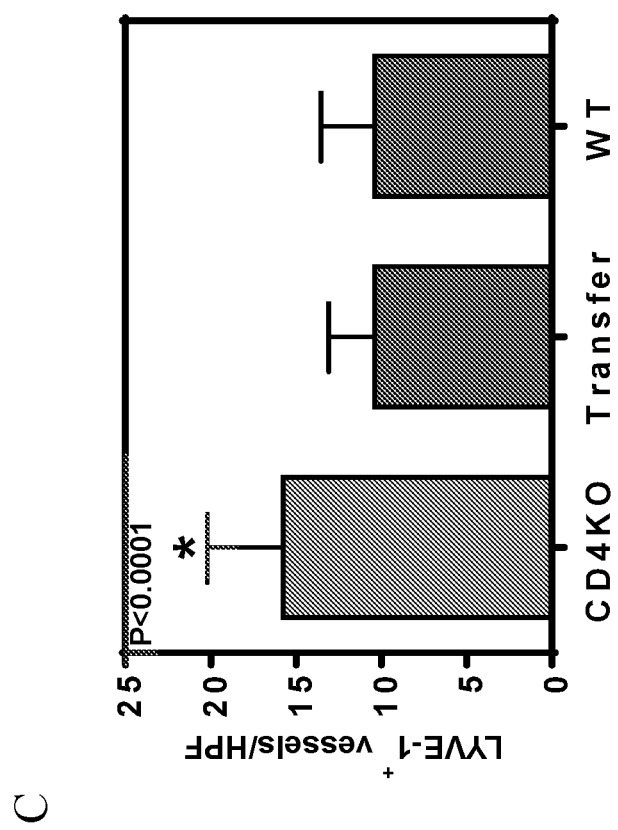
FIG. 5A-5C show that adoptive transfer of CD4+ cells impairs lymphangiogenesis and generation of lymphatic collaterals.

Adoptive Transfer of CD4+ Cells Impairs Lymphangiogenesis and Generation of Lymphatic Collaterals T cell-derived cytokines including interferon gamma, interleukin 4 and 13, and TGF-β1 have potent anti-lymphangiogenic effects. Savetsky et al., *PloS one* 10:e0126908 (2015); Shin et al.; *Nat. Comm.* 6:6196 (2015). In addition, NIR imaging studies have shown that lymphatic contractility improves over time after PLND due to lymphatic regeneration and lymphangiogenesis. Kwon et al., *PloS one* 9:e106034 (2014). Based on this background, we set out to determine how $CD4^+$ cells regulate lymphangiogenesis after lymphatic injury. Interestingly, NIR imaging of CD4KO mice 4 weeks after PLND demonstrated formation of extensive collateral vessels draining towards the inguinal lymph nodes (FIG. 5A). In contrast, Transfer and WT mice had markedly fewer collateral lymphatics after PLND. These observations were confirmed with histological sections of hind limb skin demonstrating a nearly 2-fold increase in $LYVE-1^+$ lymphatic vessels in CD4KO mice as compared with Transfer or WT (FIG. 5B-5C). Taken together, our findings suggest that $CD4^+$ cells promote lymphatic dysfunction after lymphatic injury, at least in part by causing a perilymphatic inflammatory reaction, increasing expression of iNOS with resultant decreased lymphatic pumping, and inhibiting formation of collateral lymphatics.

Example 4

Adoptively Transferred CD4+ Cells Differentiate into a Mixed Th1/Th2 Phenotype

Figure 6:
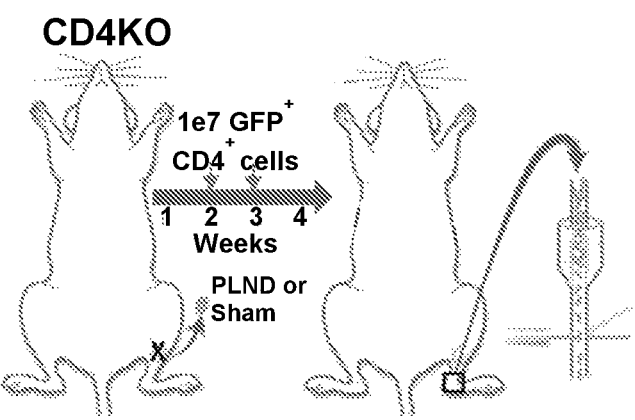
FIG. 6A-6F show that adoptively transferred CD4+ cells differentiate into a mixed Th1/Th2 phenotype.
Figure 6:
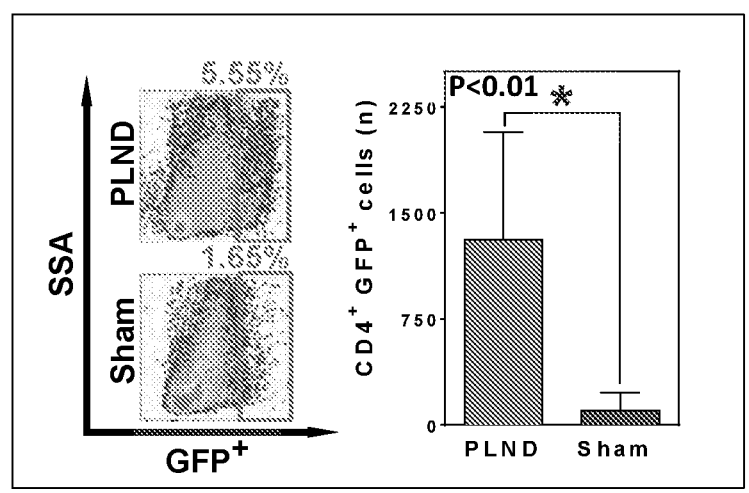
Figure 6:
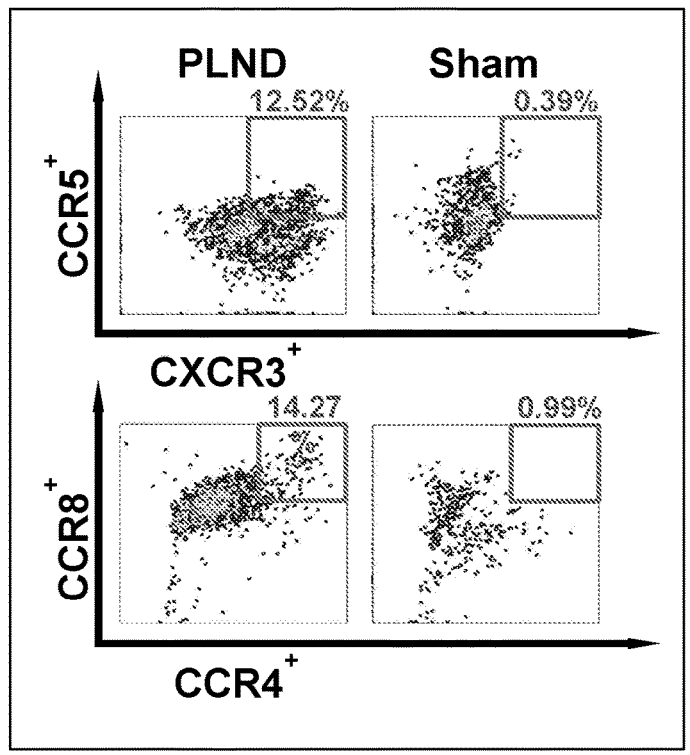
Figure 6:
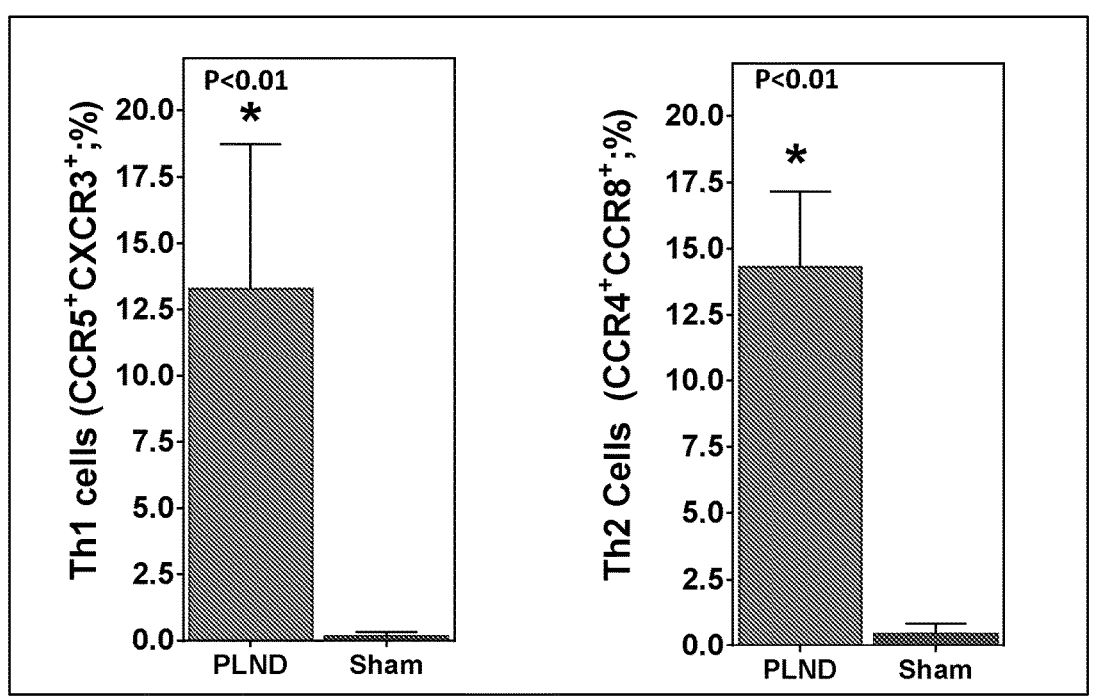
Figure 6:
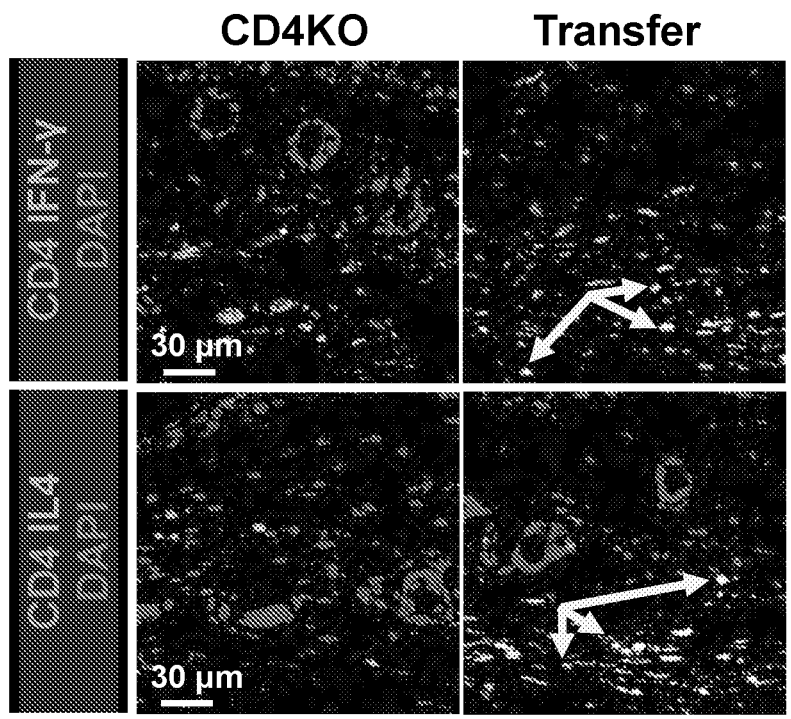
Figure 6:
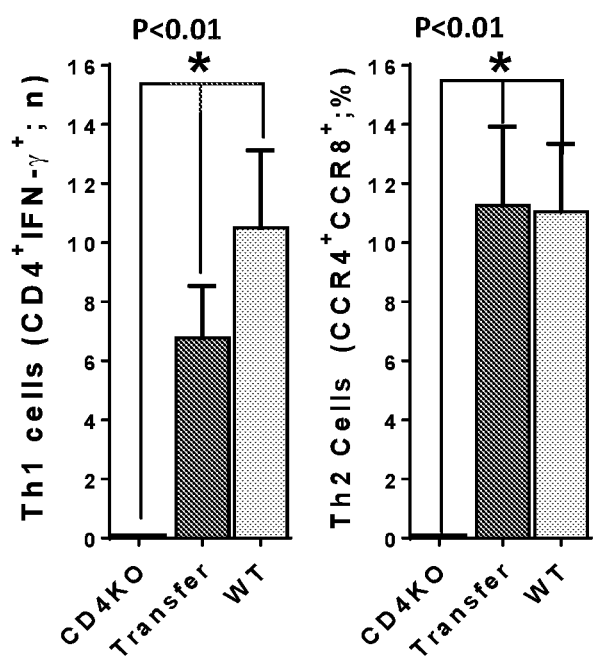

Using clinical biopsy specimens and mouse models of lymphatic injury, we have previously shown that lymphedema is associated with cutaneous infiltration of Th1 and Th2 cells. Avraham et al., *FASEB J.* 27:1114 (2013); Avraham et al., *Am. J. Pathol.* 177:3202 (2010); Zampell et al., *PloS one* 10:e0126908 (2015). To determine whether lymphatic injury promotes differentiation of naïve CD4+ cells, we performed PLND or leg skin incision without lymphadenectomy (sham) on CD4KO mice. Two weeks after surgery, animals were adoptively transferred with $1 \times 10^7$ naïve $eGFP^+$ $CD4^+$ cells once per week for 2 weeks (FIG. 6A). Consistent with our previous studies, we found that hind limb skin harvested from adoptively transferred CD4KO mice treated with PLND was infiltrated with both Th1 and Th2 differentiated $CD4^+$ cells (FIG. 6B). Flow cytometry of skin and subcutaneous tissues harvested from CD4KO animals transferred with naïve $CD4^+$ cells after PLND revealed significant increases in Th1 ($CXCR3^+$/$CCR5^+$) and Th2 ($CCR4^+$/$CCR8^+$) cells, as compared to adoptively transferred sham treated controls (96- and 51-fold increases, respectively, FIG. 6C-6D). These findings were corroborated by immunohistochemical analysis of hind limb tissues demonstrating a marked accumulation of Th1 ($CD4^+$/$IFN-\gamma^+$) and Th2 ($CD4^+$/$IL4^+$) cells in the skin/subcutaneous tissues (FIG. 6E-6F).

Example 5

Figure 7:
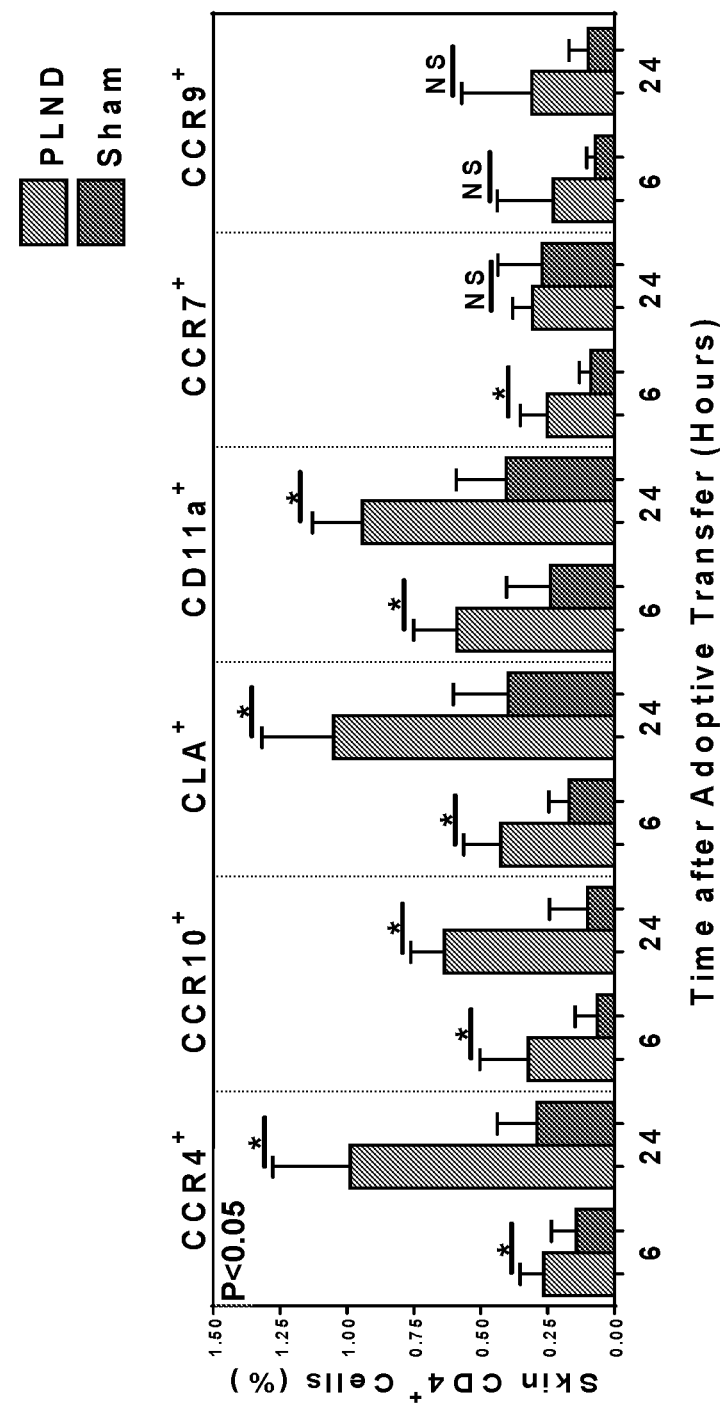
FIG. 7A-7C show that lymphatic injury results in expression of skin homing receptors on CD4+ cells and chemokines in lymphedematous skin.
Figure 7:
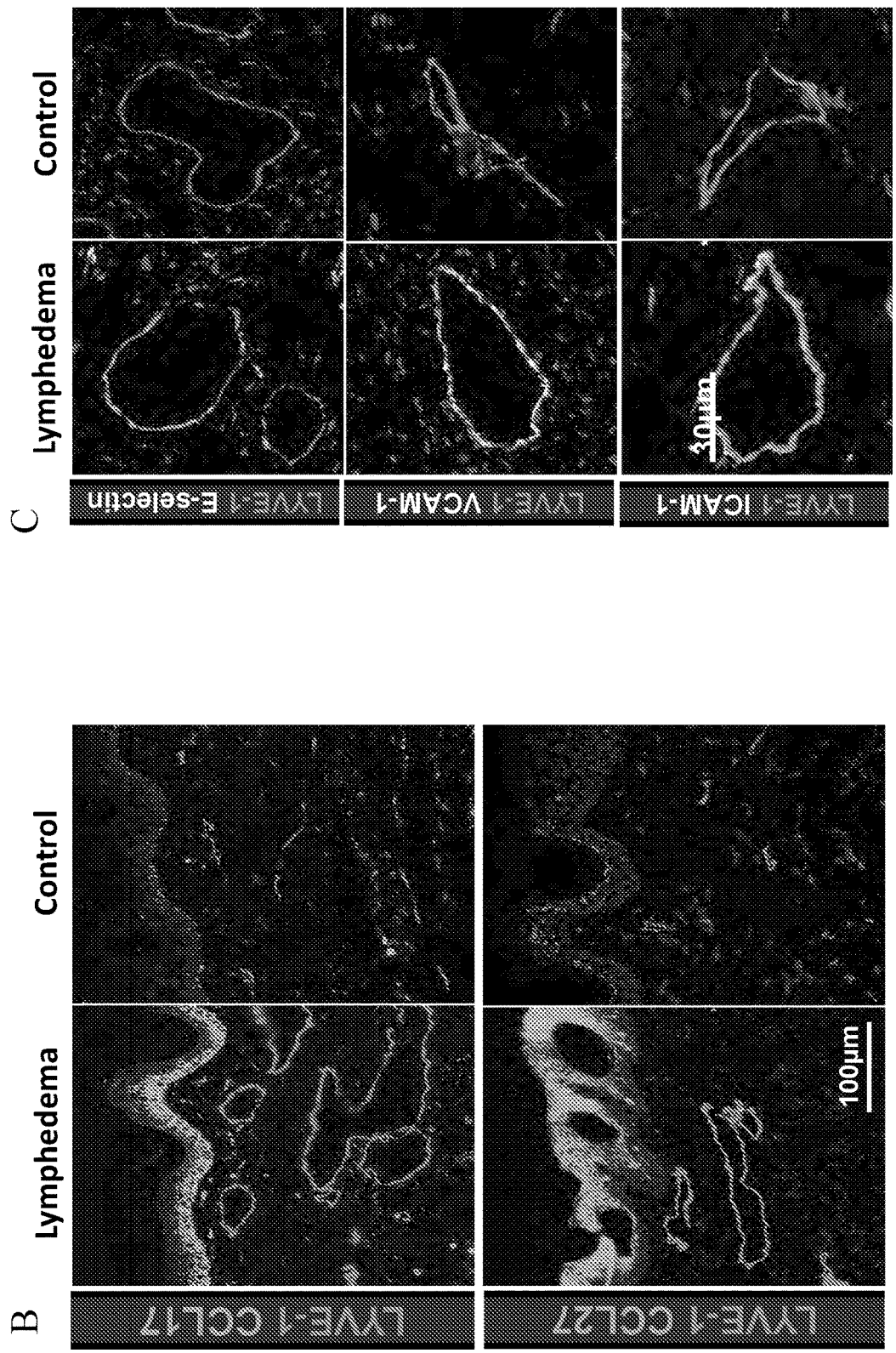
Figure 8:
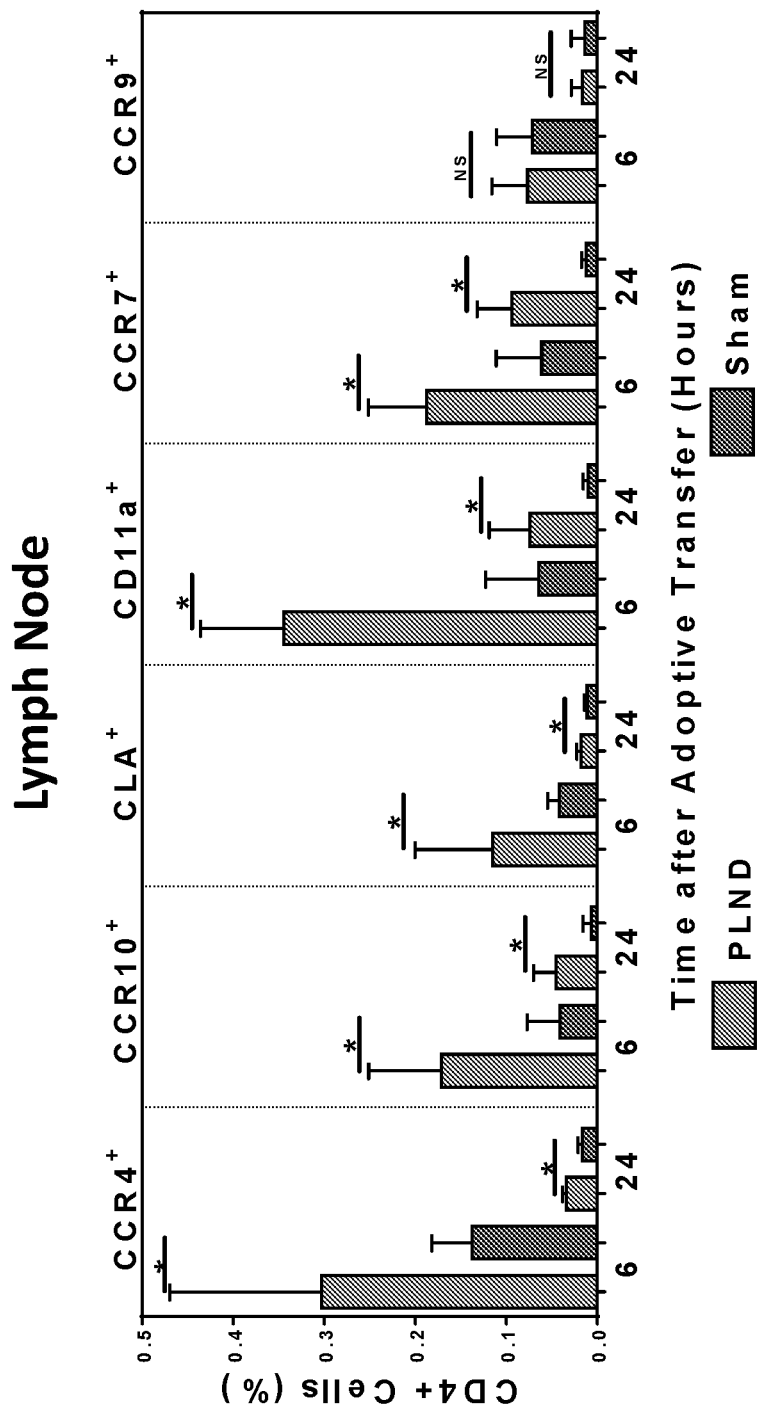
FIG. 8 shows that homing of adoptively transferred CD4+ cells to the lymph node precedes skin infiltration. Quantification of skin homing double positive CD4+ and CCR4, CCR10, CLA, and CD11a+ cells, naïve CD4+ cells (CCR7+), and intestinal homing CD4+ cells (CCR9+) in ipsilateral inguinal lymph node for PLND and Sham groups 6 hours and 24 hours after adoptive transfer. $P<0.05$ for PLND vs. Sham at 6 and 24 hours for CCR4, CCR10, CLA, CD11a, and CCR7. P=NS for PLND vs. Sham for CCR9 (6 hours and 24 hours).

Lymphatic Injury Results in Expression of Skin Homing Receptors on CD4+ Cells and Chemokines in Lymphedematous Skin Antigen-experienced effector $CD4^+$ T cells home to target tissues such as lung, gut, and skin using cell surface receptors that guide migration. Cahill et al., *J. Exp. Med.* 145:420 (1977); Scollay et al., *Eur. J. Immunol.* 6:121 (1976). For example, expression of cutaneous lymphocyte antigen (CLA), CCR4, and/or CCR10 confers the ability to home to skin, while expression of CCR9 and other cell surface receptors favors gut homing. To determine whether lymphatic injury promotes expression of skin homing receptors on CD4+ cells, we performed PLND or sham surgery on CD4KO mice, allowed them to recover for 1 week, and then adoptively transferred $1 \times 10^7$ wild-type CD4+ cells. Analysis of hind limb skin and ipsilateral inguinal lymph nodes using flow cytometry demonstrated that lymphatic injury resulting from PLND significantly increased the proportion of activated CD4+ cells that expressed skin homing receptors, as compared to sham surgical injury (FIG. 7A; FIG. 8). In addition, the percentage of CD4+ cells expressing these receptors tended to increase temporally with increased numbers of cells present in the skin 24 hours vs. 6 hours after adoptive transfer (FIG. 7A). In contrast, we found no differences between PLND and sham surgery when comparing the percentage of cells that expressed CCR7 (naïve CD4+ cells) or CCR9 (gut homing), suggesting that lymphatic injury specifically increases the expression of skin homing cell surface receptors.

Endothelial cell selectin (E-selectin) and platelet selectin (P-selectin) are ligands for CLA, and guide CD4+ cell homing to the skin via a gradient-dependent process in cutaneous inflammation. Matsumoto et al., *J. Immunol.* 175:8042 (2005); Fuhlbrigge et al., *Blood* 107:1421 (2006); Reinhardt et al., *J. Exp. Med.* 197:751 (2003); Tietz et al., *J. Immunol.* 161:963 (1998). Similarly, skin inflammation is associated with increased expression of CCL17 (the ligand for CCR4) in the epidermis, dermis, and skin capillaries, and CCL27 (the ligand for CCR10) by keratinocytes. Campbell et al., *Nature* 400:776 (1999); Homey et al., *Nat. Med.* 8:157 (2002). Leukocyte adhesion molecules such as VCAM-1 and ICAM-1 also play an important role in this process by arresting T cells in capillaries to enable transmigration into tissues. Mackay et al., *Immunol. Today* 14:99 (1993); Dustin et al., *J. Immunol.* 186:5024 (2011). To determine whether the expression of chemokine receptor ligands and adhesion molecules is increased in the setting of lymphedema, we analyzed mouse tail specimens 6 weeks after skin/lymphatic excision, and compared them with control specimens collected from mice treated with tail skin incision. We chose to study tail specimens for these experiments because the degree of chronic swelling and lymphedema in this model is much more severe than in the hind limb model. Consistent with our hypothesis that CD4+ cell homing in lymphedema is regulated by chemokine receptor expression and gradients of chemokine receptors, we found that expression of CCL17 and CCL27 was markedly increased in lymphedematous tail skin keratinocytes, as compared to sham operated animals (FIG. 7B). CCL17 was also highly expressed by keratinocytes and dermal cells that were closely associated with capillary lymphatics. Capillary lymphatics located in the dermis of lymphedematous skin also had upregulated expression of E-selectin, ICAM-1, and VCAM-1 (FIG. 7C). Taken together, our results show that lymphatic injury results in increased expression of skin homing chemokine receptors by CD4+ cells in regional lymph nodes, as well as increased expression of the ligands for these receptors in lymphedematous skin.

Example 6

Figure 9:
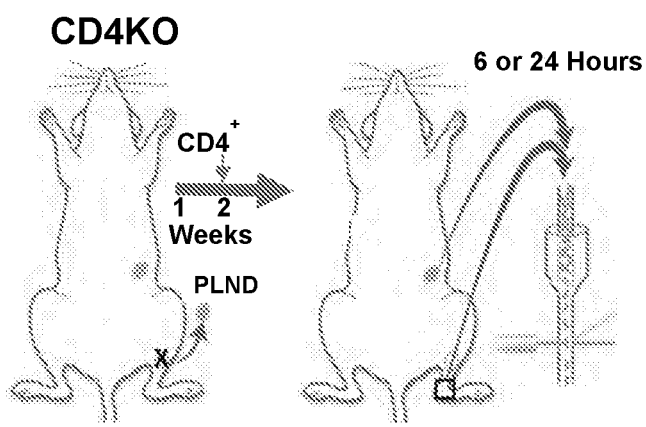
FIG. 9A-9C show that adoptively transferred CD4+ cells home to regional lymph nodes prior to skin infiltration.
Figure 9:
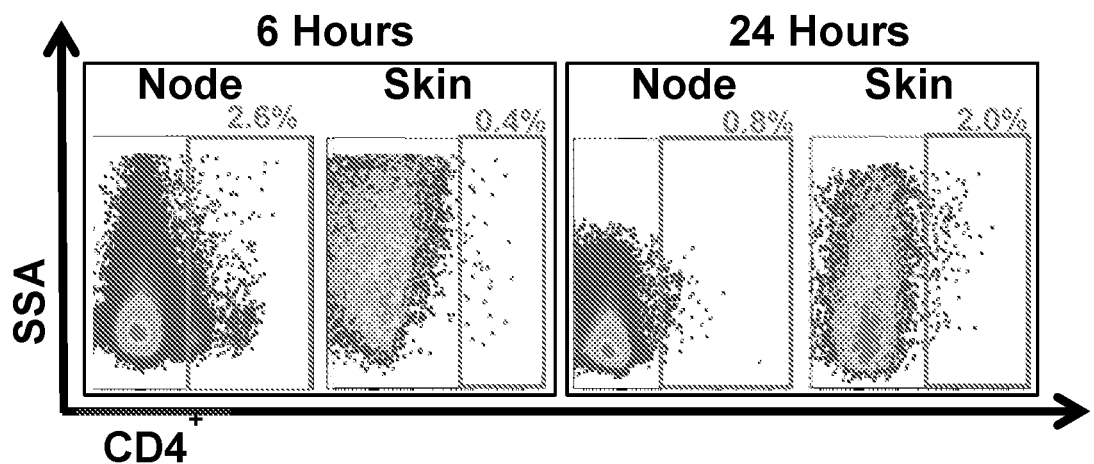
Figure 9:
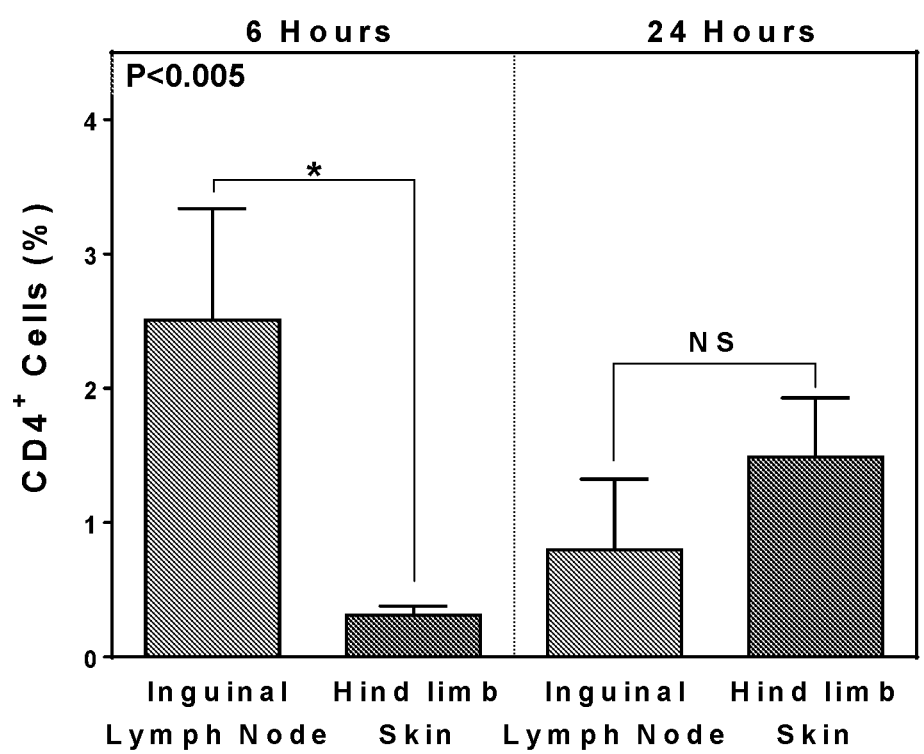

Transferred $CD4^+$ Cells Home to the Regional Lymph Node Prior to Skin Infiltration To determine the temporal sequence of CD4+ cell activation and skin homing after lymphatic injury, we compared CD4+ cell populations in the ipsilateral inguinal lymph node and hind limb skin 6 or 24 hours after adoptive transfer of CD4+ cells to CD4KO mice treated with PLND (FIG. 9A; FIG. 8). Six hours after adoptive transfer, we found nearly 7 times as many CD4+ cells in the inguinal lymph node as in the hind limb skin (FIG. 9B-9C). This difference was no longer evident at the 24 hour time point, at which time we found more CD4+ cells in the skin, although this difference did not reach statistical significance. This temporal sequence suggests, therefore, that circulating CD4+ cells are activated in the lymph node and then home to lymphedematous skin.

Example 7

Figure 10:
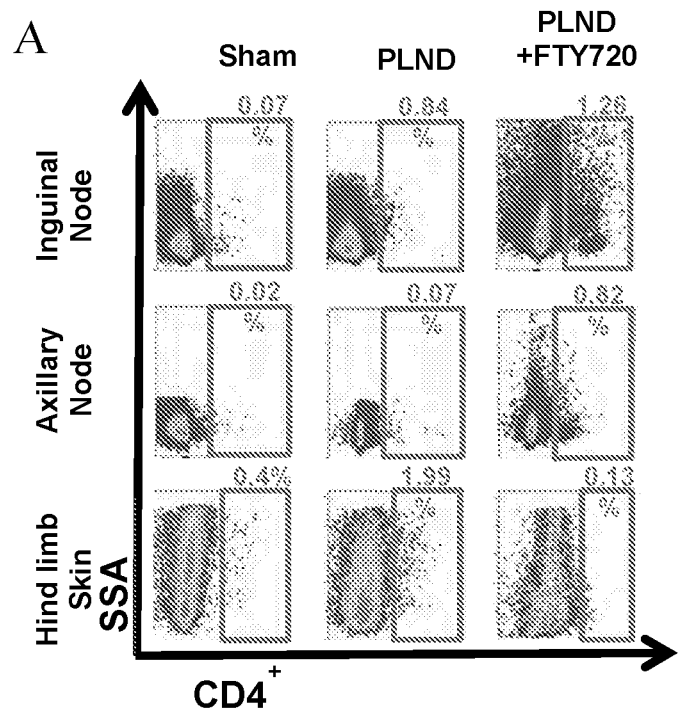
FIG. 10A-10F show that release of activated CD4+ T cells is necessary for the development of lymphedema.
Figure 10:
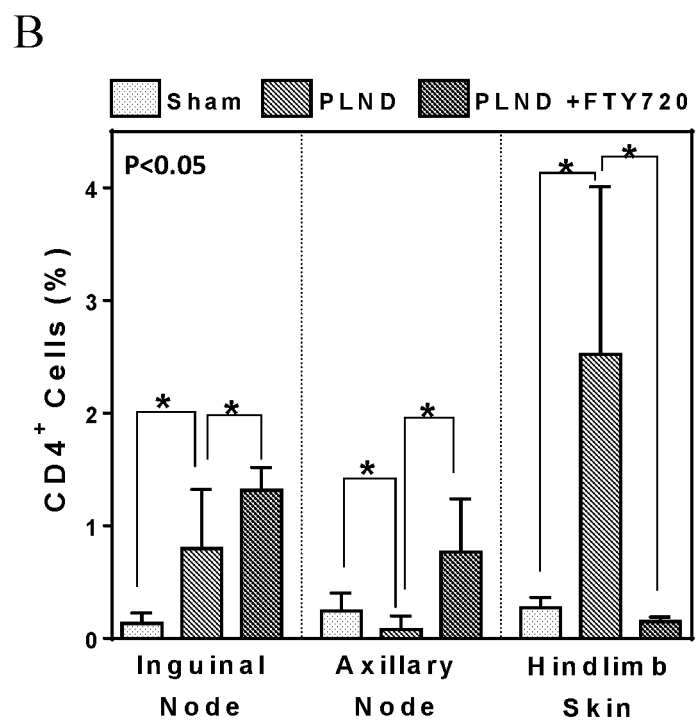
Figure 10:
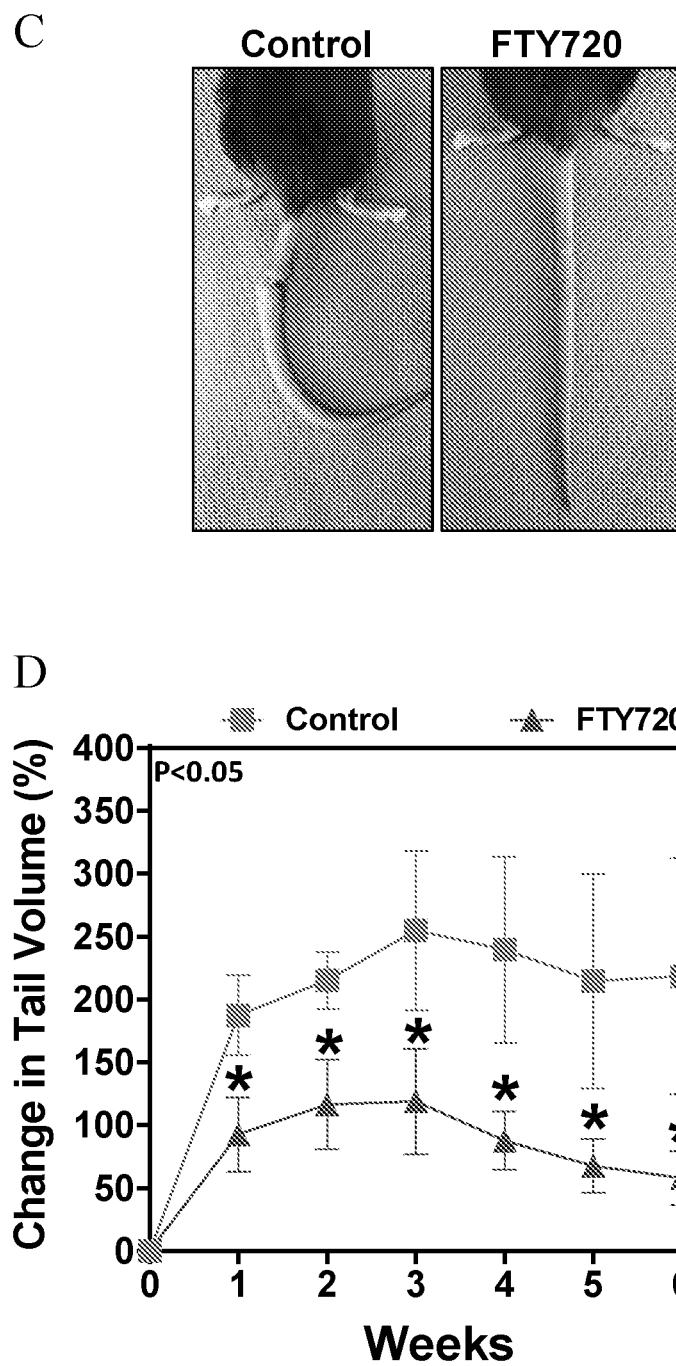
Figure 10:
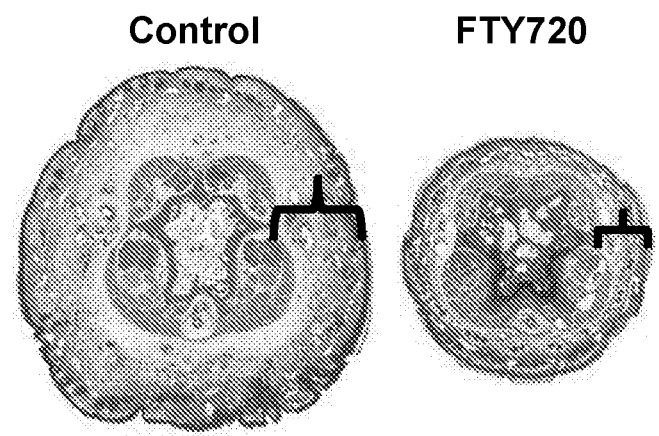
Figure 10:
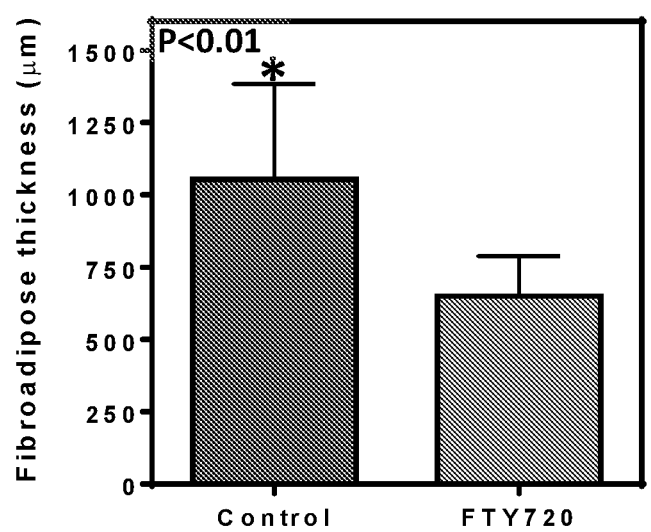

Release of CD4[+] T Cells from the Lymph Node is Necessary for Development of Lymphedema In order to prove that CD4+ cell release from the lymph node is necessary for the development of lymphedema, we next treated CD4KO mice with PLND or sham surgical excision, and treated experimental animals with FTY720, a sphingosine 1-phoshate (S1P) receptor modulator known to sequester lymphocytes in lymph nodes. Metzler et al., *Int. Immunol.* 20:633 (2008); Kharel et al., *J. Biol. Chem.* 280:36865 (2005). Control animals were treated with vehicle alone. Flow cytometry analysis of ipsilateral inguinal and axillary lymph nodes 24 hours after adoptive transfer of CD4+ cells in PLND or sham surgical animals demonstrated a significant accumulation of CD4+ cells in the inguinal but not axillary lymph nodes of animals treated with PLND (FIG. 10A-10B). This accumulation was increased significantly by the administration of FTY720, suggesting that activated T cells are sequestered in the lymph nodes. More importantly, administration of FTY720 resulted in a marked decrease in CD4+ cells in the hind limb skin after PLND, as compared with vehicle treated mice that underwent PLND.

To determine if FTY720 treatment can be useful for treating lymphedema, we next performed tail skin/lymphatic ablations on wild-type mice and treated experimental animals with FTY720 and control animals with vehicle only for 6 weeks. Gross analysis of mouse tails at this time point demonstrated markedly decreased tail swelling and fibrosis in FTY720 treated animals (FIG. 10C). These gross changes were reflected as significant decreases in tail volumes and fibroadipose deposition in FTY720 treated mice (FIG. 10D-10F). Taken together, our results suggest that circulating CD4+ cells are activated in the regional (not distant) lymph nodes, released back into the circulation, home to lymphedematous skin via cell surface receptors, and then cause pathological changes of lymphedema.

Example 8

Figure 11:
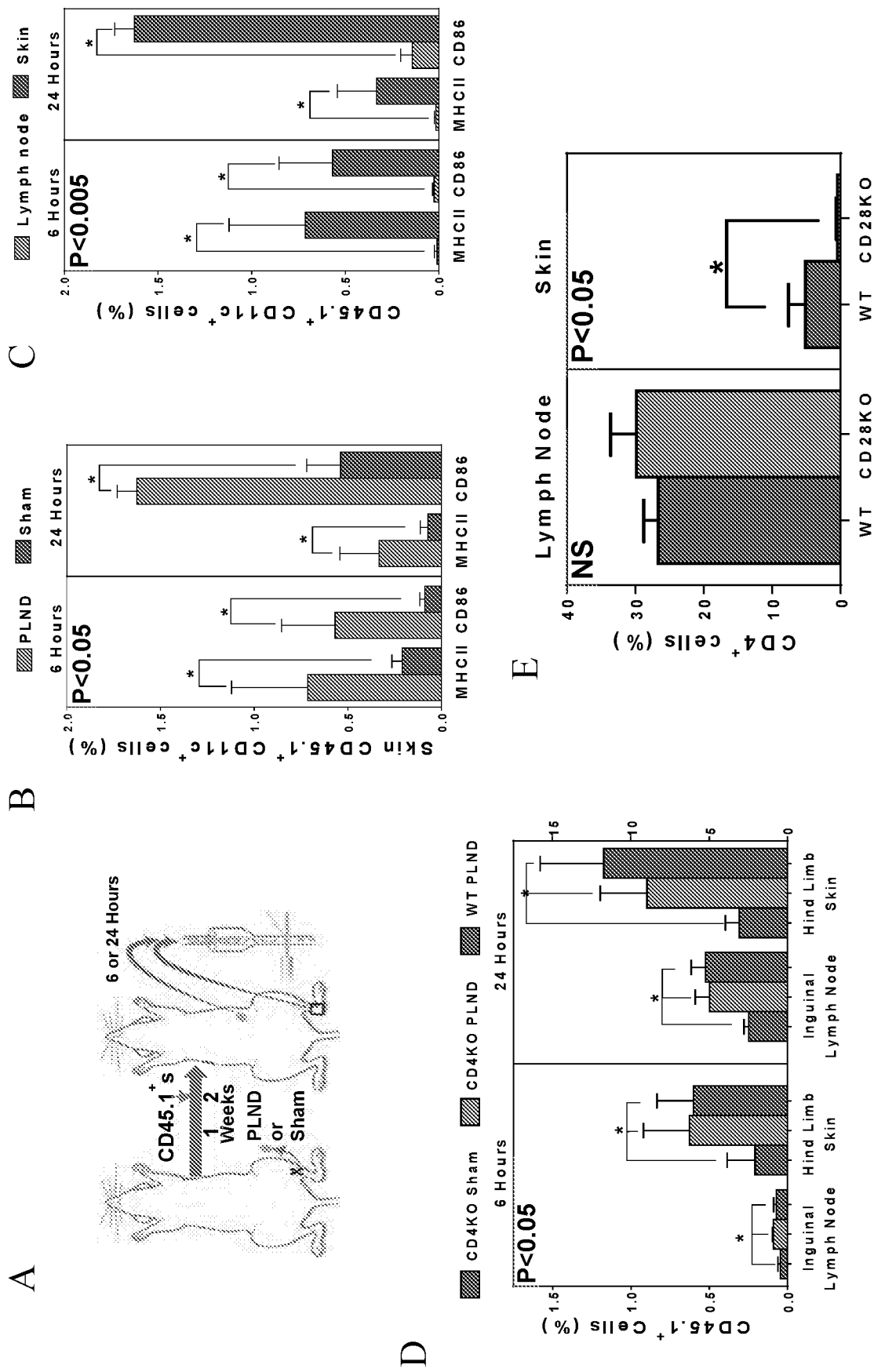
FIG. 11A-11F show that dendritic cells are activated in the site of lymphatic injury and home to skin draining regional lymph nodes where they interact with CD4+ cells.
Figure 11:
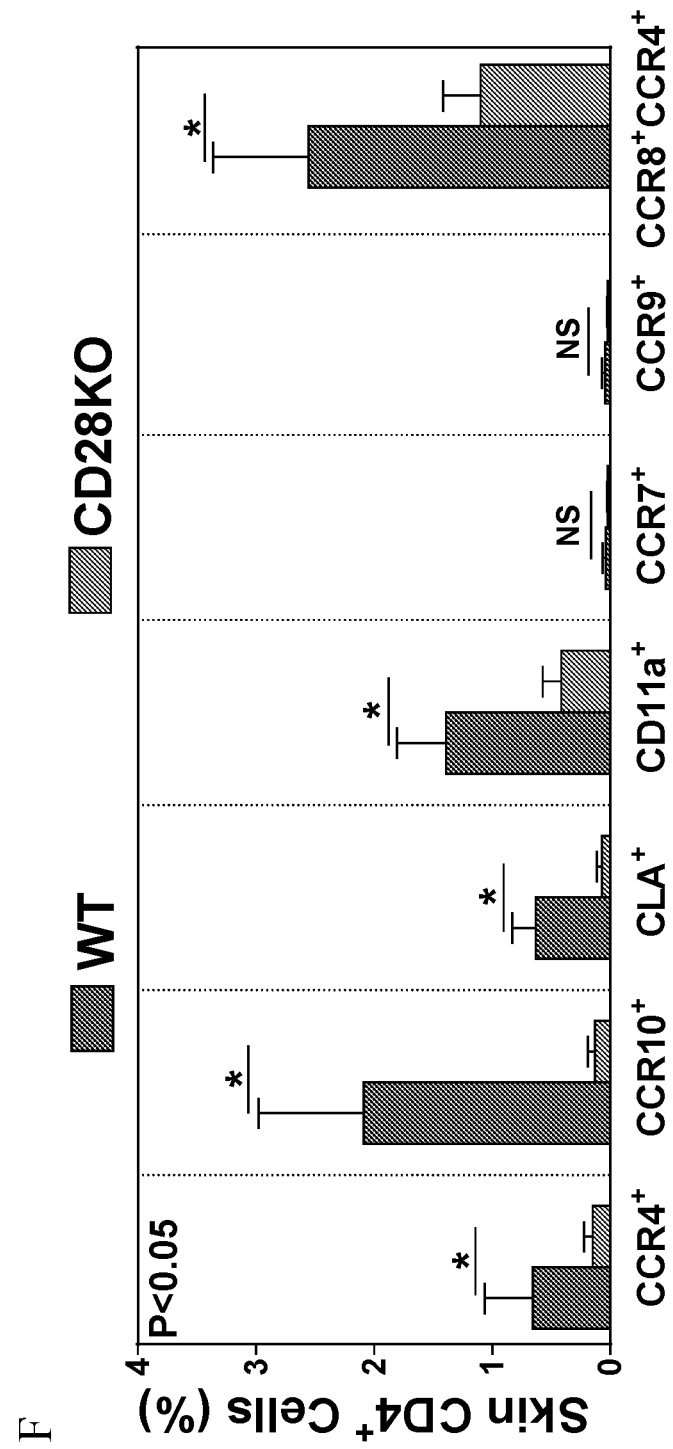

Dendritic Cells are Activated in the Site of Lymphatic Injury and Home to Skin Draining Regional Lymph Nodes where they Interact with CD4[+] Cells Dendritic cells (DCs) have a central role in the activation of tissue-trophic effector T-cell subsets. In order to study their importance in lymphedema, CD45.2[+] CD4KO or CD45.2[+] WT mice underwent PLND or sham lymph node excision and were then adoptively transferred with DCs harvested from the spleens of CD45.1+ WT donor mice (FIG. 11A). Analysis of ipsilateral hind limb skin 6 or 24 hours after adoptive transfer showed that PLND results in a significant increase (3-7 fold) in the number of activated CD45.1+ DCs (MHCII+, CD86+), as compared with sham controls (FIG. 11B). Activated DCs first appeared in the skin as early as 6 hours, and were present in this area even 24 hours after transfer (FIG. 11C). At both time points there was a higher percentage of activated donor DCs in the skin than in the draining lymph node, suggesting that systemic DCs home to lymphedematous skin where they become activated. In addition, our findings suggest that CD4+ cells are not necessary for DC activation, since activated donor DCs were noted in the skin of PLND treated CD4KO mice. This hypothesis is supported by the fact that both CD4KO and wild-type PLND treated mice had a significantly greater number of donor DCs in their skin and draining lymph nodes as compared to sham operated CD4KO mice (FIG. 11D).

DC activation of CD4+ cells in the lymph node requires both a primary signal transmitted via MHCII and a secondary signal from co-stimulatory molecules such as CD28. Therefore, to determine whether co-stimulatory molecule activation is necessary for CD4+ cell activation after lymphatic injury, we performed PLND surgery on WT and CD28KO mice, and analyzed homing chemokine receptor expression on CD4+ cells harvested from the ipsilateral hind limb skin and inguinal lymph nodes 2 weeks after surgery (FIG. 11E). Consistent with the hypothesis that DCs are necessary for activation of CD4+ cells in the lymph node after lymphatic injury, we found that CD28KO mice had markedly decreased numbers of Th2 cells (CD4[+]/CCR4+/CCR8+) and decreased percentage of skin CD4+ cells that expressed skin homing chemokine receptors. In fact, CD28KO mice treated with PLND had fewer activated CD4+ cells that expressed skin homing receptors in their ipsilateral inguinal lymph node than sham operated CD28KO mice, suggesting that co-stimulatory molecule activation by DC-CD4+ cell interaction is necessary for effector CD4+ cell differentiation and skin homing. Taken together, our findings show that circulating DCs rapidly migrate to lymphedematous tissues and become activated. These cells then traffic to regional lymph nodes where two signal interaction with T cells is necessary for T cell differentiation and expression of skin homing receptors.

Example 9

Materials and Methods

Study Design, Animal Models, and Treatments

We investigated the mechanisms that regulate CD4[+] cell activation, differentiation, and homing in lymphedema using adoptive transfer of CD4[+] cells from WT animals into CD4KO animals in two different mouse models of lymphatic injury and lymphedema. Having found that CD4[+] cells are necessary for the pathology of lymphedema, we next sought to analyze the cellular and molecular mechanisms that control this response. In subsequent examples, we tested the hypothesis that CD4[+] cells are activated by dendritic cells in the skin draining lymph nodes and home to lymphatic injury tissues, where they initiate the pathological process of lymphedema.

All experimental protocols were reviewed and approved by the IACUC committee at Memorial Sloan-Kettering Cancer Center. This institution adheres to the NIH Guide for Care and Use of Laboratory Animals and operates under the Animal Welfare Act (AWA) and Animal Scientific Procedures Act of 1986. Female C57BL/6J (WT), CD4eGFP (B6.NOD-Tg(Cd4-EGFP)1Lt/J), CD4 knockout mice (B6.12952-Cd4tm1Mak/J, CD4KO), CD28 knockout (36.12952-Cd28tm1Mak/J; CD28KO), and Pep Boy (36.SJL-Ptprca Pepcb/BoyJ) (Jackson Laboratories, Bar Harbor, Me.) were maintained in a pathogen free, temperature and light controlled environment. Each experiment was performed using a minimum of 6-8 animals, and assays were performed in triplicate. All cell counts were performed by reviewers blinded to the intervention.

To induce lymphedema, we used a mouse tail model in which a 5 vmm portion of the mid-tail is excised and the deep lymphatic collecting vessels are ligated. Avraham et al., *Am. J. Pathol.* 177:3202 (2010); Clavin et al., *Am. J. Physiol. Heart Circ. Physiol.* 295:H2113 (2008); Rutkowski et al., *Microvasc. Res.* 72:161 (2006); Tabibiazar et al., *PloS Med* 3:e254 (2006). This model reliably results in sustained tail swelling, severe impairment in lymphatic function, and histopathologic features consistent with clinical lymphedema, lasting as long as 10 weeks after surgery. Avraham et al., Am. J. Pathol. 177:3202 (2010); Clavin et al., *Am. J. Physiol. Heart Circ. Physiol.* 295:H2113 (2008); Rutkowski et al., *Microvasc. Res.* 72:161 (2006); Tabibiazar et al., *PloS Med* 3:e254 (2006). In other experiments, animals were randomized to either PLND or sham surgery. PLND was performed as previously reported, removing the nodes, surrounding fat pad, and afferent/efferent lymphatics. Control animals underwent sham popliteal surgeries where a skin incision was made in the area of the popliteal lymph node without nodal resection. Although sustained lymphedema is not observed here, it has previously been described as a means of analyzing regeneration of collateral lymphatics and collecting lymphatic pumping capacity. Proulx et al., *Biomaterials* 34:5128 (2013); Sharma et al., *Am. J. Physiol. Heart and Circul. Physiol.* 292:H3109 (2007).

In other experiments, WT mice underwent tail or popliteal lymphatic ablation surgeries and were subsequently randomized to treatment with FTY720 (Sigma Aldrich, St. Louis, Mo.), an SW receptor modulator that blocks lymphocyte egress from lymph nodes. Metzler et al., *Int. Immunol.* 20:633 (2008); Kharel et al., *J. Biol. Chem.* 280:36865 (2005). Briefly, FTY720 was dissolved in water as per the manufacturer's recommendations, and supplied ad libitum starting the day of lymphatic ablation. Mice received an estimated 1.25 mg/kg/day for 2 or 6 weeks (for PLND or tail surgeries, respectively) until tissues were harvested. Water was changed every 3 days.

Animals were excluded from the study and sacrificed if wound infection or skin ulceration was observed. When performing experiments that required anesthesia, mice were anesthetized using isofluorane. Respiratory rate and tail pinching were used to monitor the depth of anesthesia. At the conclusion of the experiment, animals were euthanized by carbon dioxide asphyxiation as recommended by the American Veterinary Medical Association.

Bone Marrow Transplantation

Bone marrow transplantation was performed using standard techniques. Peinado et al., *Nat. Med.* 18:883 (2012). Briefly, recipient animals underwent total body irradiation with 950 rads ($^{137}CS$) using a whole animal irradiator (Nordion Gammacell 40, Best Theratronics Ltd., Ottawa, Canada). Twenty four hours later, bone marrow was harvested from donor mice tibiae and femurs, filtered through a 100 μm cell strainer (Falcon, San Jose, Calif.), and 5×10$^6$ cells were infused into recipient mice via a tail vein injection. Mice were allowed to recover for 4 weeks before experiments were performed.

$CD4^+$ Cell Isolation, Expansion, and Adoptive Transfer $CD4^+$ T cells were isolated from the spleens of donor WT and $CD4^+$ eGFP mice using magnetic beads and negative selection according to the manufacturer's recommendations (Miltenyi Biotec, Auburn, Calif.). Isolated $CD4^+$ and $CD4^+$ eGFP T cells were culture expanded using a modification of previously reported techniques. Harrington et al., *Nat. Immunol.* 6:1123 (2005). Briefly, cells were cultured with RPMI and supplemented with 2 μg/mL anti-CD28 (eBiosciences, San Diego, Calif.) and 100 U/mL of IL-2 (Roche Diagnostics, Indianapolis, Ind.) in 48-well plates coated with 4 μg/mL anti-CD3b antibody (eBiosciences San Diego, Calif.). To maintain a naïve $CD4^+$ cell (i.e., Th0) phenotype, cells were also incubated with 10 μg/mL anti-IFN-R Ab (Clone XMG; R&D Systems, Minneapolis, Minn.) and 10 μg/mL anti-IL-4 Ab (Clone 11811; Sigma-Aldrich, St. Louis, Mo.). Flow cytometry for CD4, CD44, and CD68 was performed on cultured cells to assess maturity.

Culture expanded naïve $CD4^+$ cells ($1\times10^7$) were suspended in 100 μL of sterile phosphate buffered saline (PBS) and adoptively transferred to CD4KO mice by weekly retro-orbital sinus injections beginning two weeks after surgery for 2 or 4 weeks (for PLND or lymphatic tail ablation, respectively), followed by sacrifice. Control animals were injected with a similar volume of PBS. Delivery of $CD4^+$ cells was confirmed using flow cytometry to quantify $CD4^+$ cells in single cell suspensions created from spleens and aortic lymph nodes. Similarly, $CD4^+$ eGFP or CD4 cells were adoptively transferred once to CD4KO mice 2 weeks after popliteal lymph node resection or sham surgeries.

In other experiments, CD11c+ cells were isolated from CD45.1+ Pep Boy female mice as per the manufacturer's recommendations (Miltenyi Biotec, Auburn, Calif.) and adoptively transferred into CD4KO or WT mice 2 weeks after PLND or sham surgeries.

Flow Cytometry

Flow cytometry was performed using a modification of our published methods. Mehrara et al., *FASEB J.* 24:4877 (2010). Briefly, a 5 mm portion of skin/subcutaneous tissue was harvested at a point located 1 cm distal to the site of tail lymphatic ablation or popliteal lymph node resection. Single cell suspensions were created by digestion with collagenase D, DNAse I, and Dispase (all from Roche Diagnostics, Indianapolis, Ind.). Single cell suspensions from the spleen and lymph node were isolated by mechanically rupturing the lymphoid tissue, lysing RBCs, and filtering. For flow cytometry, endogenous Fc receptors were blocked with Fc block (CD16/CD32; eBiosciences, San Diego, Calif.), and single stains were performed using flow cytometric beads (Miltenyyi Biotec, Auburn, Calif.). Cells suspensions were stained using fluorophore-conjugated antibodies for the following cell surface markers: CD45, CD3, CD4, CCR4, CCR9, CD11a, CLA, CD86, MHCII, CD11c, CD45.1, CD45.2 (all from Biolegend, San Diego, Calif.), CXCR3, CCR5 (both from eBiosciences, San Diego, Calif.), CCR7 (BD Biosciences, San Jose, Calif.), CCR8 and CCR10 (both from RandD Systems, Minneapolis, Minn.). Flow cytometry was performed using a Fortessa flow cytometer with BD FACSDiva™ software (BD Biosciences; San Jose, Calif.). Data was analyzed with FlowJo software (Tree Star, Ashland, Oreg.).

Tail Volume, Lymphoscintigraphy, In Vivo Lymphatic Imaging

Tail volumes were calculated weekly using the truncated cone formula. Clavin et al., *Am. J. Physiol. Heart Circ. Physiol.* 295:H2113 (2008). Lymphoscintigraphy was performed to analyze uptake of technetium ($^{99m}Tc$) after peripheral injection. Avraham et al., *FASEB J.* 27:1114 (2013); Clavin et al., *Am. J. Physiol. Heart Circ. Physiol.* 295:H2113 (2008). Briefly, $^{99m}Tc$ sulfur colloid was injected into the distal tail, and decay-adjusted uptake in the sacral lymph nodes was performed using an X-SPECT camera (Gamma Medica, Northridge, Calif.). Region-of-interest analysis was performed using ASIPro Software (CTI Molecular Imaging, Knoxville, Tenn.) to calculate peak and rate of nodal uptake. Clavin et al., *Am. J. Physiol. Heart Circ. Physiol.* 295:H2113 (2008).

Lymphatic collecting vessel pumping function was assessed using a modification of previously published techniques. Proulx et al., *Biomaterials* 34:5128 (2013); Proulx et al., *Angiogenesis* 16:525 (2013). Briefly, mice were anesthetized with inhalational anesthesia, and 0.15 mg/mL indocyanine green (Sigma-Aldrich, St. Louis, Mo.) was injected intradermally in the dorsum of the hind limb. Images were captured using an EVOS EMCCD camera (Life Technologies, Carlsbad, Calif.) and a LED light source (CoolLED, Andover, UK) mounted on a Zeiss V12 Stereolumar microscope (Caliper Life Sciences, Hopkinton, Mass.). Lymphatic pumping function was analyzed using Fiji software (NIH, Bethesda, Md.).

Histology and Immunohistochemistry

Histology was performed using our published techniques. Avraham et al., *FASEB J.* 27:1114 (2013). Primary antibodies used included Collagen I, CD45, CD4, podoplanin, LYVE-1 (R&D Systems, Minneapolis, Minn.), α-SMA (Sigma-Aldrich, St. Louis, Mo.), interleukin 4 (IL4), interferon gamma (IFN-γ), chemokine ligands 17 and 27 (CCL17 and CCL27), E-selectin (CD62E), vascular cell adhesion protein 1 (VCAM-1), intracellular adhesion molecule 1 (ICAM-1), transforming growth factor beta 1 (TGF-β1), and inducible nitric oxide synthase (INOS) (all from Abcam, Cambridge, Mass.). All secondary antibodies for immunohistochemistry were obtained from Vector Laboratories (Burlingame, Calif.). For immunofluorescent staining we used Alexafluor fluorophore-conjugated secondary antibodies (Life Technologies, Carlsbad, Calif.). Slides were scanned using a Mirax slide scanner (Zeiss, Munich, Germany). Cell counts were performed on high-powered sections (40-80×) in 5-6 animals per group, 4 high-power fields/animal, by 2 blinded reviewers. Type I Collagen deposition was quantified as a ratio of positively stained dermis and subcutaneous tissues within a fixed threshold to total tissue area, in 4 sections/animal/group, in 40× high-power fields, using MetaMorph® Offline Software (Meta-Morph Inc., Nashville, Tenn.). and is expressed using arbitrary units. Ehrlich et al. *Am. J. Radial.* 145:105 (1994).

Subcutaneous adipose tissue thickness measurements were analyzed by 2 blinded reviewers (n=5-6 animals/group) using standardized cross-sections by measuring from the width of tissues bounded by the reticular dermis to the deep fascia in 4 standardized regions per section. Capillary lymphatic vessel area was quantified as previously described using Panoramic viewer software (3DHistech, Budapest, Hungary) in four 40× high-power fields/animal per group. Avraham et al., *FASEB J.* 27:1114 (2013).

Statistical Analysis

Statistical analysis was performed using GraphPad Prism (GraphPad Software, Inc., San Diego, Calif.) software. Student's T-test was used to compare differences between 2 groups, while multi-group comparisons were performed using analysis of variance (ANOVA) with post hoc tests for individual group comparisons. Data are presented as mean±standard deviation unless otherwise noted; $p<0.05$ was considered significant.

* * *

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

The invention claimed is:

1. A method of treating or preventing lymphedema, the method comprising administering to a subject having lymphedema or susceptible to developing lymphedema a composition comprising an effective amount of a sphingosine 1-phosphate (S1P) receptor inhibitor.

2. The method of claim 1, wherein the S1P receptor inhibitor is selected from the group consisting of FTY720 (Fingolimod), ONO-4641 (Ceralifimod), RPC1063 (Ozanimod), ACT-128800 (Ponesimod), BAF312 (Siponimod), LT1009 (Sonepcizumab), AAL-R ((R)-2-amino-4-(4-heptyloxyphenyl)-2-methylbutanol), CS-0777 ((R)-1-(5-(3-amino-4-hydroxy-3-methylbutyl)-1-methyl-1H-pyrrol-2-yl)-4-(p-tolyl)butan-1-one), KRP-203 (2-amino-2-propanediol), RP-001 (N-[4-[5-[3-Cyano-4-(1-methylethoxy)phenyl]-1,2,4-oxadiazol-3-yl]-2,3-dihydro-1H-iden-1-yl]-β-alanine), and Syl930.

3. The method of claim 1, wherein the S1P receptor inhibitor is FTY720.

4. The method of claim 1, wherein the composition is administered orally.

5. The method of claim 1, wherein the composition is administered intravenously.

6. The method of claim 1, wherein the subject is a human.

7. The method of claim 1, wherein the lymphedema results from abnormal development of the subject's lymphatic system.

8. The method of claim 1, wherein the subject has sustained a lymphatic injury.

9. The method of claim 1, wherein the composition is administered prophylactically within about six weeks of a lymphatic injury.

10. The method of claim 8, wherein the lymphatic injury is congenital.

11. The method of claim 8, wherein the lymphatic injury results from removal, ligation, or obstruction of lymph nodes or lymph vessels.

12. The method of claim 8, wherein the lymphatic injury results from surgery, trauma, fibrosis of lymph tissue, an infection, or a burn.

13. The method of claim 12, wherein the surgery is joint replacement surgery.

14. The method of claim 1, wherein the subject has undergone or is undergoing treatment for cancer.

15. The method of claim 14, wherein the treatment is surgery.

16. The method of claim 14, wherein the treatment is chemotherapy.

17. The method of claim 14, wherein the treatment is radiation.

18. The method of claim 14, wherein the cancer comprises a solid tumor.

19. The method of claim 1, wherein the lymphedema is chronic lymphedema.

20. The method of claim 1, wherein the method comprises administering to the subject a second active agent.

21. A method for inhibiting infiltration of $CD4^+$ cells into the skin of a subject, the method comprising administering to the subject an effective amount of a sphingosine 1-phosphate (S1P) receptor inhibitor.

22. The method of claim 21, wherein the S1P receptor inhibitor is FTY720.

* * * * *